(12) United States Patent
Blilou et al.

(10) Patent No.: US 12,740,522 B2
(45) Date of Patent: Sep. 22, 2026

(54) HIGH-THROUGHPUT, MODULAR, PORTABLE, LIVE-IMAGING ROOT SYSTEM AND METHOD

(71) Applicant: KING ABDULLAH UNIVERSITY OF SCIENCE AND TECHNOLOGY, Thuwal (SA)

(72) Inventors: Ikram Blilou, Thuwal (SA); Vinicius M. Lube, Thuwal (SA); Alexander Przybysz, Thuwal (SA); Khaled Nabil Salama, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 374 days.

(21) Appl. No.: 18/696,072

(22) PCT Filed: Oct. 4, 2022

(86) PCT No.: PCT/IB2022/059467
§ 371 (c)(1),
(2) Date: Mar. 27, 2024

(87) PCT Pub. No.: WO2023/057900
PCT Pub. Date: Apr. 13, 2023

(65) Prior Publication Data

US 2025/0017159 A1 Jan. 16, 2025

Related U.S. Application Data

(60) Provisional application No. 63/252,769, filed on Oct. 6, 2021.

(51) Int. Cl.
*A01H 4/00* (2006.01)
*G01N 33/00* (2006.01)

(52) U.S. Cl.
CPC ............... *A01H 4/008* (2013.01); *A01H 4/00* (2013.01); *G01N 33/0098* (2013.01)

(58) Field of Classification Search
CPC ....... A01H 4/008; A01H 4/00; G01N 33/0098
See application file for complete search history.

(56) References Cited

U.S. PATENT DOCUMENTS 6,845,860 B1 * 1/2005 Walker .................. B65G 47/53 198/817
2014/0030802 A1 * 1/2014 Eberle .................. C12M 41/14 435/317.1

(Continued)

FOREIGN PATENT DOCUMENTS

WO WO-2017174348 A1 * 10/2017 ............ C12M 23/10
WO WO-2020211926 A1 * 10/2020 ............ A01G 31/06

OTHER PUBLICATIONS

Atkinson, J.A., et al., "Uncovering the Hidden Half of Plants Using New Advances in Root Phenotyping," Current Opinion in Biotechnology, Feb. 2019, Vo. 55, pp. 1-8, Elsevier.

(Continued)

*Primary Examiner* — Samir A Ahmed
(74) *Attorney, Agent, or Firm* — PATENT PORTFOLIO BUILDERS PLLC

(57) ABSTRACT

A portable, modular plant monitoring system includes an imaging subsystem configured to acquire images of plural plants with a camera, an imaging actuation subsystem configured to support the imaging subsystem and to translate the imaging subsystem, a carousel system having a carousel configured to hold the plural plants in plural petri dishes, a carousel actuation subsystem configured to support the carousel system, to translate the carousel and to rotate the carousel, a support subsystem configured to hold the camera actuation subsystem and the carousel actuation subsystem, and a control subsystem configured to coordinate (1) a (Continued)

movement of the camera, (2) a linear movement and a rotation of the carousel, (3) image acquisition by the camera, and (4) image processing to detect a characteristic of the plural plants.

20 Claims, 22 Drawing Sheets

(56) References Cited

U.S. PATENT DOCUMENTS

2016/0192607 A1* 7/2016 Kitagawa ............... A01G 31/06 47/62 N
2020/0240906 A1* 7/2020 Waxman ............ G01N 21/3504

OTHER PUBLICATIONS

Bagley, S.A., et al., "Low-Cost Automated Vectors and Modular Environmental Sensors for Plant Phenotyping," Sensors, Jun. 11, 2020, vol. 20, No. 11, pp. 1-15.
Brochure for MultipleXLab, Robotic Root Imager, downloaded Oct. 3, 2022 (www.multiplex-lab.com).
Brochure for PlantScreen Systems, PSI (Photon Systems Instruments) spol. s.r.o, downloaded Sep. 15, 2022 (www.plantphenotyping.com).
Clark, R.T., et al., "Three-Dimensional Root Phenotyping with a Novel Imaging and Software Platform1[C][W][OA]," Plant Physiology, Mar. 31, 2011, vol. 156, pp. 455-465.
Granier, C., et al., "Phenopsis, an Automated Platform for Reproducible Phenotyping of Plant Responses to Soil Water Deficit in Arabidopsis Thaliana Permitted the Identification of an Accession with Low Sensitivity to Soil Water Deficit," New Phytologist, Nov. 25, 2005, vol. 169, pp. 623-635.
International Search Report in corresponding/related International Application No. PCT/IB2022/069467, date of mailing Jan. 10, 2023.
Jeudy, C., et al., "RhizoTubes as a New Tool for High Throughput Imaging of Plant Root Development and Architecture: Test, Comparison with Pot Grown Plants and Validation," Plant Methods, Jun. 7, 2016, vol. 12, No. 31, pp. 1-18, Springer.
Li, D., et al., "High-Throughput Plant Phenotyping Platform (HT3P) as a Novel Tool for Estimating Agronomic Traits From the Lab to the Field," Frontiers in Bioengineering and Biotechnology, Jan. 13, 2021, Vo. 8, Article 623706, pp. 1-24.
Lien, M.R., et al., "A Low-Cost and Open-Source Platform for Automated Imaging," Plant Methods, Jan. 28, 2019, vol. 15, No. 6, pp. 1-14.
Men, Y., et al., "A High-Throughput Imaging System to Quantitatively Analyze the Growth Dynamics of Plant Seedlings," Integrative Biology, Jun. 12, 2012, vol. 4, Issue 8, pp. 945-952.
Nagel, K.A., "The Platform GrowScreen-Agar enables Identification of Phenotypic Diversity in Root and Shoot Growth Traits of Agar Grown Plants," Plant Methods, Jun. 23, 2020, vol. 16, pp. 1-17.
Nagel, K.A., et al., "Growscreen-Rhizo is a Novel Phenotyping Robot Enabling Simultaneous Measurements of Root and Shoot Growth for Plants Grown in Soil-Filled Rhizotrons," Functional Plant Biology, Jun. 7, 2012, pp. 1-14, CSIRO Publishing.
Subramanian, R., et al., "A High Throughput Robot System for Machine Vision Based Plant Phenotype Studies," Machine Vision and Applications, 2013, vol. 26, pp. 619-636, Springer.
Vadez, V., et al., "LeasyScan: A Novel Concept Combining 3D Imaging and Lysimetry for High-Throughput Phenotyping of Traits Controlling Plant Water Budget," Journal of Experimental Botany, Jun. 1, 2015, vol. 66, No. 18, pp. 5581-5593, Oxford University Press.
Written Opinion of the International Searching Authority in corresponding/related International Application No. PCT/IB2022/069467, date of mailing Jan. 10, 2023.
Wu, J., et al., "RhizoChamber-Monitor: A Robotic Platform and Software Enabling Characterization of Root Growth," Plant Methods, Jun. 7, 2018, vol. 14, No. 44, pp. 1-15.
Zhao, C., et al., "Crop Phenomics: Current Status and Perspectives," Frontiers in Plant Science, Jun. 3, 2019, vol. 10, Article 714, pp. 1-16.

* cited by examiner

| Genotype | Germination index (%) | Growth rate (mm/h) | *N* |
|---|---|---|---|
| WT | 96 | 0.15672[a] | 53 |
| *scr* | 98 | 0.13240[b] | 55 |
| *Rbi* | 98 | 0.11503[b] | 51 |
| *shr* | 74 | 0.03135[c] | 28 |

FIG. 12A

| Genotype | Germination index (%) | Growth rate (mm/h) | *N* |
|---|---|---|---|
| WT | 100 | 0.17367[a] | 56 |
| *jkd4* | 95 | 0.13914[a] | 53 |
| *wox5* | 96 | 0.15751[a] | 52 |
| *trycpc* | 80 | 0.14568[a] | 45 |

FIG. 12B

| Genotype | Germination index (%) | Growth rate (mm/h) | *N* |
|---|---|---|---|
| WT | 92 | 0.11854[b] | 57 |
| *aux1* | 94 | 0.15267[a] | 60 |
| *lax3* | 53 | 0.09149[c] | 34 |
| *pin2* | 100 | 0.08241[c] | 64 |
| *pin2aux1* | 100 | 0.07152[c] | 61 |

FIG. 12C

| Genotype | Germination index (%) | Growth rate (mm/h) | *N* |
|---|---|---|---|
| WT | 94 | 0.14602[b] | 60 |
| *e2fa-1* | 80 | 0.12230[c] | 51 |
| *cdkb1;1cdkb1;2* | 100 | 0.09782[d] | 59 |
| *cycd2;1* | 78 | 0.16982[a] | 49 |

FIG. 12D

HIGH-THROUGHPUT, MODULAR, PORTABLE, LIVE-IMAGING ROOT SYSTEM AND METHOD

CROSS-REFERENCE TO RELATED APPLICATIONS

This application is a U.S. National Stage Application of International Application No. PCT/IB2022/059467, filed on Oct. 4, 2022, which claims priority to U.S. Provisional Patent Application No. 63/252,769, filed on Oct. 6, 2021, entitled "MULTIPLEXLAB: A HIGH-THROUGHPUT MODULAR PORTABLE LIVE-IMAGING ROOT PHENOTYPING PLATFORM," the disclosures of which are incorporated herein by reference in their entirety.

BACKGROUND

Technical Field

Embodiments of the subject matter disclosed herein generally relate to a system and method for monitoring, visualizing and analyzing the real time growth of plants in their natural environment, and more particularly, to a platform that holds plural plants, provides nutrients and water to the plants, and simultaneously allows an imaging device to obtain real time information about the plants.

Discussion of the Background

Optical imaging is an essential facet of monitoring, studying, and understanding plant related events. In the fields of biology and biomedicine, multiscale live imaging is routinely used to visualize growth, morphogenesis, and plant responses to multiple stressors and diseases. The most used systems are stereomicroscopes coupled with digital cameras. Although these systems are easy to operate and images can be captured rapidly, they are expensive, often heavy, not very portable, and their setup is not flexible. Moreover, they allow only one mode of imaging because the camera is mounted on either vertical or horizontal stages. These restrictions limit their usage in fields where samples need to be captured dynamically, for example, at diverse locations, for example, fields with growing crops and trees, or archeological samples or remains found at historical sites. Moreover, these systems are often not affordable for research institutions or farming related corporations with limited financial resources.

Optical imaging is often used for selecting crops with enhanced productivity, disease resistance, and smart water consumption. With the global increase in food demand, selecting crops that perform well is critical to improving food production. Breeding for better crops includes selecting seeds and/or plants with desirable phenotypic traits. However, isolating plants with particular phenotypes, accurately and nondestructively, is still challenging because it involves analyzing hundreds to thousands of samples and sometimes selecting specific complex features at multiscale levels ranging from the cell, tissue, and organ to the whole plant.

Many platforms are available to achieve multimodal and multidimensional phenotyping. These platforms can operate in a wide range of conditions ranging from controlled and semi-controlled environments to field conditions [1, 2]. High-throughput phenotyping is performed primarily at the organism and organ levels and has a limited resolution. Examples of these platforms include PlantScreen™ Systems, which is equipped with a three-dimensional (3D) laser and multispectral camera and has a range of instruments that allow phenotyping in growth chambers, greenhouses, and in the field [3]. Some systems can also phenotype the roots grown in either Rhizotrons [4] or Rhizotubes [5]. The PlantEye can automatically image and compute multiple above-ground features in a nondestructive way [6]. Other platforms are tailored to more specific traits, such as Phenopsis, which monitors the plant response to a water deficit. In addition, LiDAR is a creative system for high-throughput phenotyping in the field. Additional platforms have also been valuable for live imaging. The 3D root growth and imaging system allows high-throughput phenotyping of rice root traits at the seedling stage [8]. RhizoChamber is a robotic platform used to analyze root growth in rhizoboxes [9]. The system integrates hardware and software to analyze the spatio-temporal dynamics of root growth from time-course images of multiple plants. Although these systems allow high-throughput phenotyping, they are costly.

Another attractive system to noninvasively monitor root growth is the X-ray Computed Tomography, which allows 3D root phenotyping in soil [10]. However, the system does not allow high-throughput phenotyping, the resolution is low and is also costly. Recently, efforts have been put forward to establish alternative approaches for low-cost live imaging of plants under stress conditions [11, 12]. For higher magnification imaging, the most commonly used systems are costly stereomicroscopes coupled with digital cameras.

Thus, there is a need for an inexpensive system capable of live monitoring the growth of the plants in their medium and automatically analyzing the simultaneous feature changes in a large number of plants.

BRIEF SUMMARY OF THE INVENTION

According to an embodiment, there is a portable, modular plant monitoring system that includes an imaging subsystem configured to acquire images of plural plants with a camera, an imaging actuation subsystem configured to support the imaging subsystem and to translate the imaging subsystem along a first horizontal axis X and along a vertical axis Z, a carousel system having a carousel configured to hold the plural plants in plural petri dishes, wherein the carousel has a number of identical external, side faces, a carousel actuation subsystem configured to support the carousel system, to translate the carousel along a second horizontal axis Y, which is perpendicular on the first horizontal axis X and the vertical axis Z, and to rotate the carousel about the vertical axis Z, a support subsystem configured to hold the camera actuation subsystem and the carousel actuation subsystem, and a control subsystem configured to coordinate (1) a movement of the camera along the first horizontal axis X and the vertical axis Z, (2) a movement of the carousel along the second horizontal axis Y and a rotation about the vertical axis Z, (3) image acquisition by the camera, and (4) image processing to detect a characteristic of the plural plants.

According to another embodiment, there is a carousel system for holding seeds, and the carousel system includes plural petri dishes configured to hold the seeds, and a carousel having plural stages stacked on top of each other, each stage having plural external, side faces, and each external, side face being configured to hold a corresponding petri dish. Each stage includes a base frame and plural columns configured to be removably attached to the base frame and define slots to hold the petri dishes.

According to yet another embodiment, there is a method for automatically monitoring plant growth, and the method includes placing plural petri dishes into a carousel of a plant monitoring system, each petri dish holding plural seeds, controlling a number of images taken per hour or minutes by a camera of the plural petri dishes, rotating the carousel so that each petri dish is imaged by the camera at a given first time interval, vertically moving the camera so that each stage of the carousel is imaged by the camera at a given second time interval, wherein the stages are stacked on top of each other, providing light to each petri dish in the carousel, where a duration of the light, and a wavelength of the light are dynamically selected by a control subsystem, supplying water to the petri dishes first stage of the carousel, and controlling a temperature of the petri dishes in a second stage of the carousel with plural temperature-controlled elements.

BRIEF DESCRIPTION OF THE DRAWINGS

For a more complete understanding of the present invention, reference is now made to the following descriptions taken in conjunction with the accompanying drawings, in which:

FIG. 12A illustrates the germination index and growth rate of root stem cells for regulator mutants, FIG. 12B illustrates the germination index and growth rate of root stem cells for patterning mutants, FIG. 12C illustrates the germination index and growth rate of auxin transport mutants, and FIG. 12D illustrates the germination index and growth rate of cell-cycle regulator mutants;

DETAILED DESCRIPTION OF THE INVENTION

Figure 1:
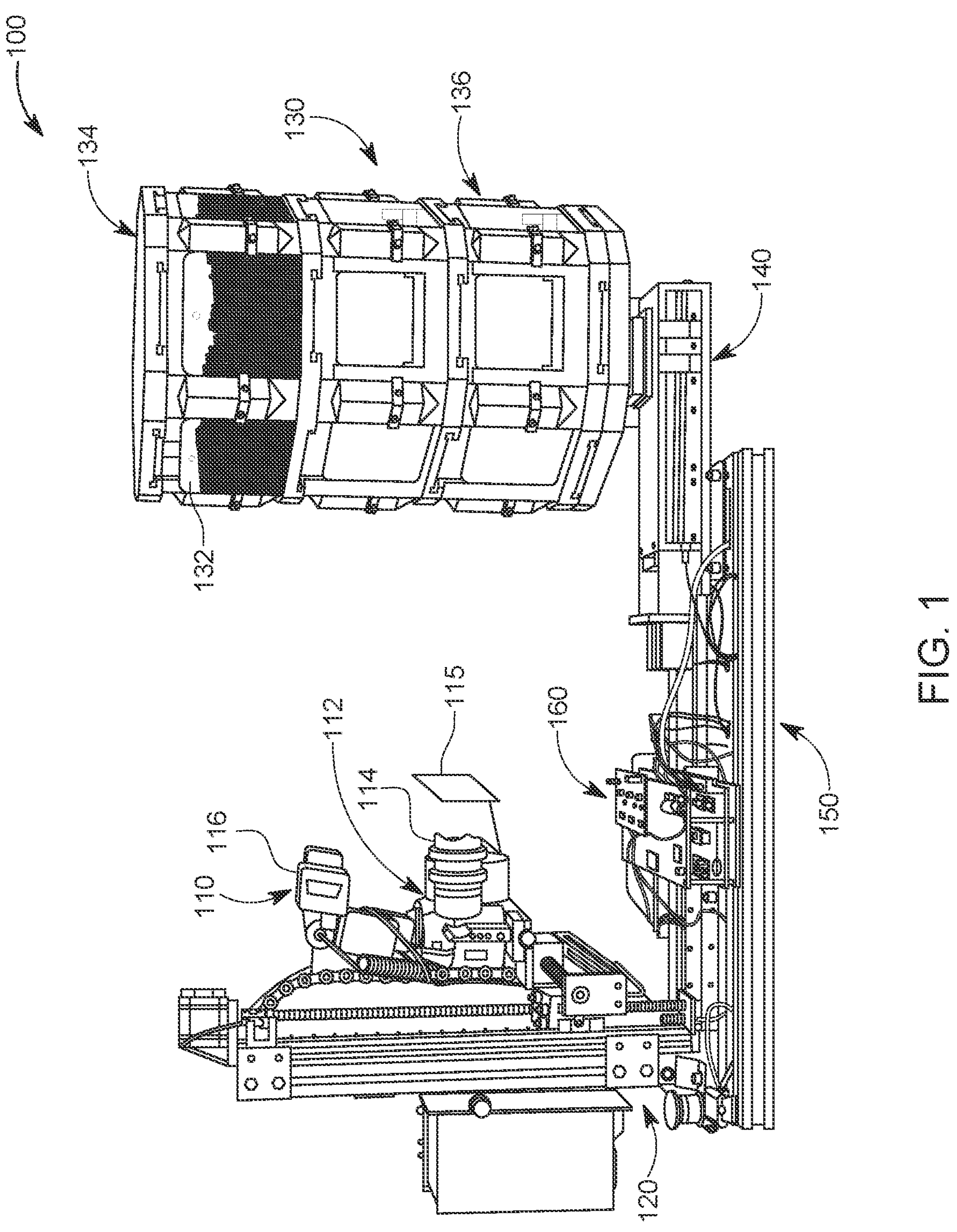
FIG. 1 is a schematic diagram of a high-throughput, portable, modular, live-imaging system for monitoring the grow of seeds.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a three-stage carousel that is modular and portable and is accompanied by an imagining system for acquiring images of seeds and their roots. However, the embodiments to be discussed next are not limited to a three-stage carousel or to studying seeds, but may be applied to a carousel with any number of stages and to organism other than seeds.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel imaging and seed holding platform includes a system that combines high-throughput phenotyping with high-resolution imaging. The system, called herein "MultipleXLab system" can be used as a single-plate system to monitor biological processes at a high resolution. MultipleXLab is an optical, modular imaging setup for high-throughput phenotyping of seed germination and early root growth on agar and soil plates. In one application, the MultipleXLab system may be based on off-the-shelf, low-cost, portable camera components that are modified and adapted to noninvasively capture dynamic processes in living biological systems. The system includes at least one digital camera and 3D-printed multiplate holders with integrated growth LED lighting. Users of the system can simultaneously capture 18 square petri dish plates containing multiple specimens, allowing noninvasively screening of up to thousands of seedlings to monitor germination rates and root-growth dynamics. In one application, the system can acquire and analyze up to 100 images per hour, with each image capturing up to 64 seeds or roots, which allows automated imaging of thousands of Arabidopsis and hundreds of tomato seedlings growing on agar plates at a high resolution. In this or another application, computer-vision and pattern recognition technologies were implemented, combined with machine learning, to automatically analyze and quantify distinct phenotypes, and also to calculate growth rates.

As discussed later, the MultipleXLab system has exceptional resolution for imaging worms, soil nematodes, insect behavior, and feeding habits in natural habitats. The system is highly flexible and can be adapted to perform dual-axis imaging of single plates, allowing both vertical or horizontal camera/lens orientations simply by flipping the entire setup without the need to unscrew or turn a knob. The MultipleXLab system can be used for mutant screening, where millions of seeds must be scored for a particular phenotype.

FIG. 1 shows an overview of the MultipleXLab system 100 (also called a "plant monitoring system" or simply called herein the "system") having an imaging subsystem 110, an imaging actuation subsystem 120, a plant holding carousel subsystem 130, a carousel actuation subsystem 140, a support subsystem 150, and a control subsystem 160. The imaging subsystem 110 may include a camera 112. The camera 112 may be, in one application, a modified digital Canon 5DSr SLR camera (Canon Inc., Tokyo, Japan) with a 50.1 Megapixels full-frame sensor (36×24 $mm^2$) devoid of a low-pass filter, which is replaced by a full spectrum filter made from fused silica. The camera 112 may be attached to a Canon EF 40 mm f/2.8 STM lens stacked 114 on a 2:1 teleconverter (Vivitar Series 1). This specific configuration provides a unique 28 degrees angle of view at 30 cm away to cover the entire view (150 $cm^2$) of the petri dish 132, as well as to permit proper lighting and larger magnification of 0.24× (opposed to 0.18×) life size, given by a 15 cm gain in minimum focus distance. A set of band-pass filters 115, including infra-red, visible light, and ultra-violet can be used in front of the lens element to narrow the spectrum of interest.

Figure 2:
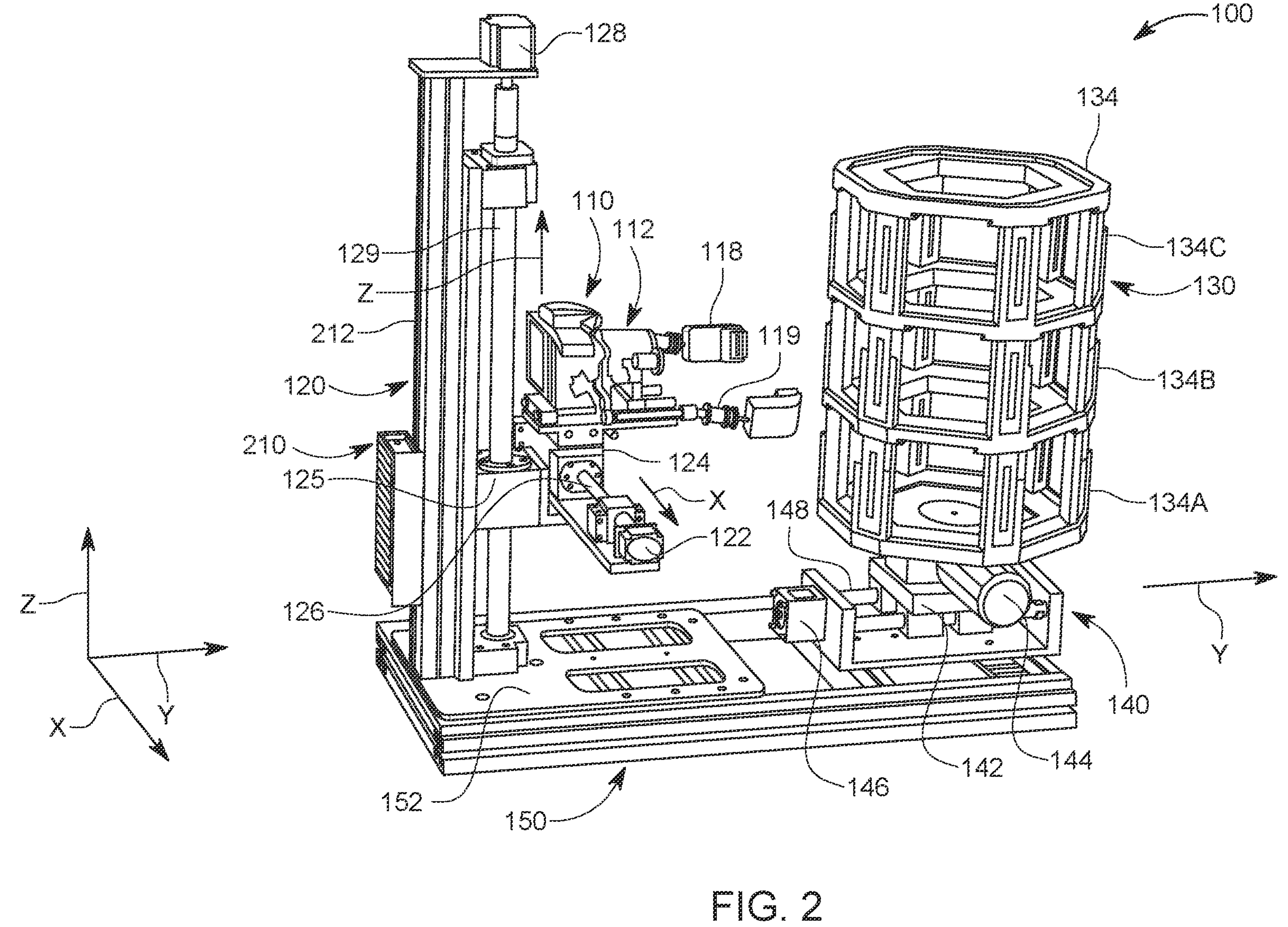
FIG. 2 is a schematic diagram of the system shown in FIG. 1, with a stackable and modular carousel shown without petri dishes.

In one application, a flashlight 116 may be attached to the lens 114, and two flashes 118, see FIG. 2, diffused with a strap-on light softbox can be used. The flashes 118 may be mounted on articulated arms 119 so that these external flashes provided oblique and diffuse lighting on the specimens in the petri dish 132, as well as to assist in high magnification imaging when high intensity light is required. FIG. 2 presents the system 100 with less equipment so that selected parts are better viewed. The imaging subsystem 110 is attached to the imaging actuation subsystem 120, which is configured to displace the imaging subsystem 110 along a vertical axis Z, and also along a horizontal axis X, as schematically illustrated in FIG. 2. The imaging actuation subsystem 120 includes a first motor 122 that controls the movement of a support base 124 along the X axis. The imaging subsystem 110 may be attached to the support base 124. The first motor 122 may be connected to a screw type axel 126 so that a rotation of the screw-type axel makes the support base 124 to move along or against the X axis. Similarly, the imaging actuation subsystem 120 may include a second motor 128, which is connected to another screw-type axel 129, and a rotation of the screw-type axel 129 makes the entire support base 124 to move along or against the Z axis. The support base 124 may be attached to the screw-type axel 129 through a bridge 125, as shown in FIG. 2.

A power source 210 may be attached to a vertical support element 212, which is configured to hold the second motor 128 and the vertical axel 129. With this arrangement, the imaging actuation subsystem 120 is capable to move the camera 112 vertically and horizontally, as instructed by the control subsystem 160 (not shown in FIG. 2). In one application, the power source 210 includes two distinct power sources, a first for supporting the active cooling/heating, and a second power supply for the remaining controls system, namely, lighting elements and the flash of the camera 112, the control subsystem 160, and the various motors used by the actuation sub-systems. In one application, the imaging actuation sub-system 120 can be detached from the support subsystem 150 and turned on a side, so that the vertical axel 129 becomes horizontal and the horizontal axel 126 becomes vertical, so that a position of the camera 112 is flipped on the side. FIG. 1 shows that the imaging sub-system 110 and the imaging actuation sub-system 120 are electrically connected to the control subsystem 160 so that a processor of the control subsystem can instruct the camera to shoot at a desired time interval, and also to actuate the first and second motors 122 and 128 to move the camera to image each petri dish of the carousel subsystem 130.

The plant holding carousel subsystem 130 includes a carousel 134 configured to hold plural petri dishes 132. The carousel 134 is shown in FIG. 2 emptied of any petri dishes 132 and having a hexagonal cross-section in a horizontal plane. Other shapes may be used, for example, square, pentagon, etc. FIG. 1 shows the carousel 134 filled with plural petri dishes in each stage. It is noted that the carousel has all the petri dishes located in its external side faces 136. The carousel may be made to have any number of identical external, side faces 136. In one application, each side face 136 holds at least one petri dish 132. The carousel 134 in FIGS. 1 and 2 has three-stages 134A to 134C, placed on top of each other. The first or bottom stage 134A is attached to a moving base 142, which belongs to the actuation carousel subsystem 140. The moving base 142 is attached to a vertical axel (not shown), which is connected to a third motor 144. When the processor of the control subsystem 160 instructs the third motor 144 to rotate, the moving base 142 rotates and implicitly the carousel 134 rotates, so that various petri dishes 132 from the same stage are exposed to the camera 112. The actuation carousel subsystem 140 also includes a fourth motor 146, which rotates a horizontal axel 148, which is attached to the rotating base 142. When this happens, the rotating base 142 is moved closer or further away from the camera 112, along the axis Y, as shown in FIG. 2. Note that the movement of the camera 112 along the Z direction due to the second motor 128 makes the camera to image petri dishes from different stages 134A to 134C, and the movement of the camera along the axis X due to the first motor 122, makes the camera to focus on a desired area of a given petri dish. The movement of the carousel along the Y axis allows the camera to change its focus while the rotation of the carousel allows each petri dish to be imaged by the camera 112. Thus, with the four motors discussed herein, the camera and the carousel can be adjusted to image any area of any petri dish located on any stage in any position on the carousel.

Figure 3:
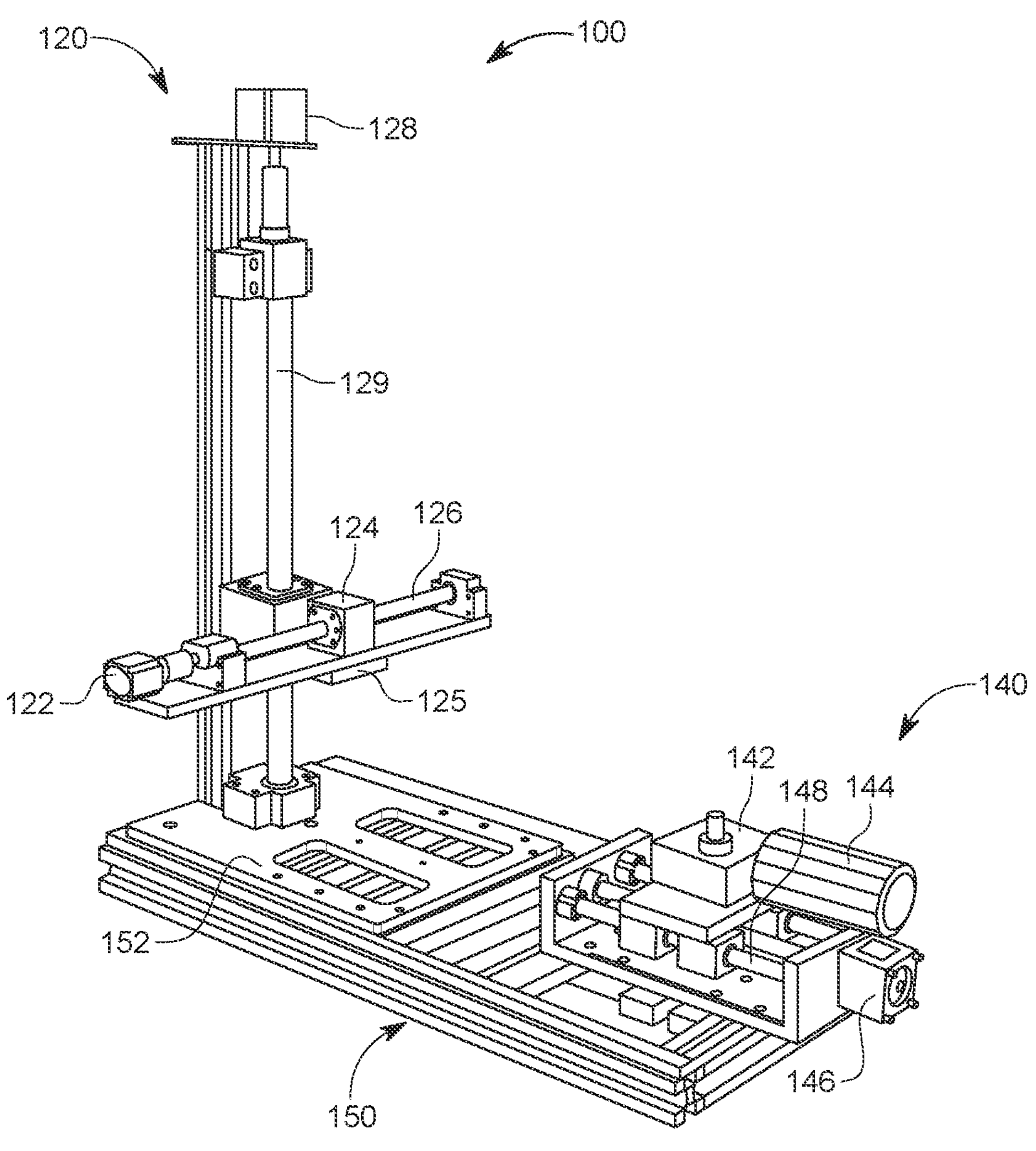
FIG. 3 illustrates actuation subsystems and a rail mechanism for handling the carousel and a camera subsystem.

FIG. 2 shows the entire imaging actuation subsystem 120 being fixedly attached to a base 152 of the support subsystem 150, and the entire carousel actuation subsystem 140 also being fixedly attached to the support subsystem. The support subsystem 150 may be made of any solid material, for example, aluminum, steel, composite material, polymers etc. FIG. 3 shows the two actuation systems 120 and 140 being attached to the support subsystem 150 without the interference from the carousel subsystem or the imaging subsystem.

Figure 4:
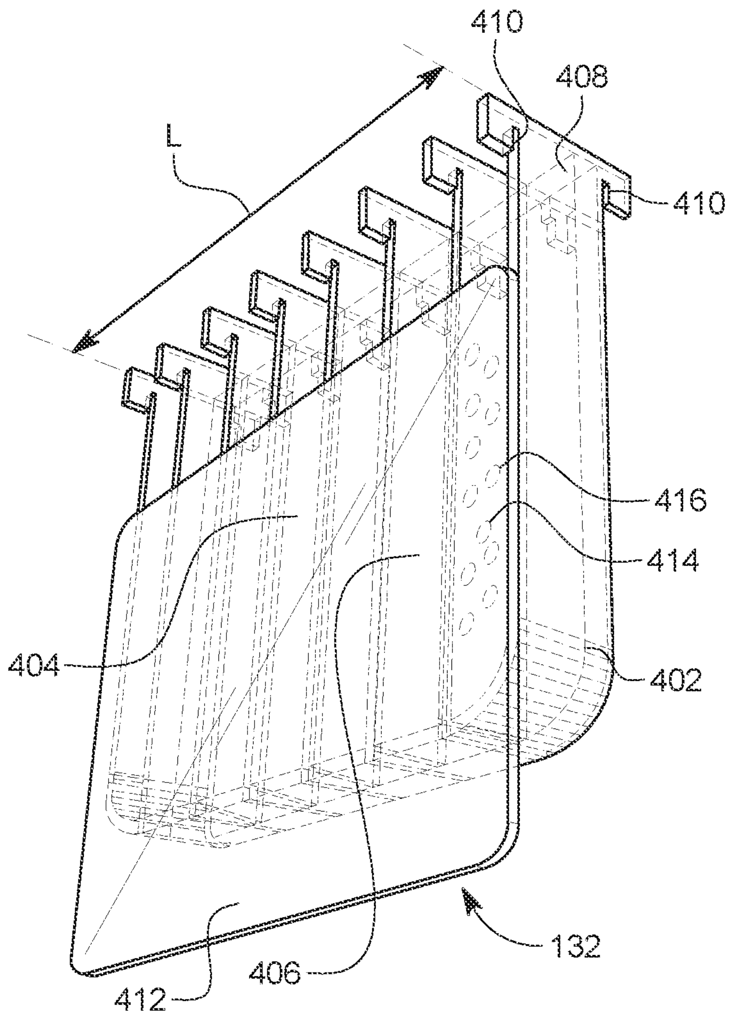
FIG. 4 schematically illustrates a petri dish that can be added to the carousel to hold the seeds.

The plant holding carousel subsystem 130 is now discussed in more detail. FIG. 4 shows the body 402 of a petri dish 132 being configured with plural separation walls 404 so that plural chambers 406 are defined within each single petri dish. Thus, each chamber may hold different seeds from the next chamber. The body 402 may be 3D printed. The body ends with plural fingers 408 and each end of the fingers 408 may have one or two recesses 410, for receiving a flat and transparent face 412. When the flat and transparent face 412 is attached to one side of the body 402 and another plate (transparent or not) is attached to the opposite side of the body, and both are engaged in the recesses 410 so that the petri dish 132 is fully closed. Thus, soil 414 and seeds 416 may be placed in the petri dish 132 as shown in FIG. 4, and the petri dish may be placed in one open slot in the carousel 134, as show in FIG. 1. In one embodiment, the entire petri dish may be made of a transparent material, for example, plastic or glass. In yet another embodiment, only the face 412 may be made of the transparent material. The petri dish may be 3D printed if desired. A length L of the petri dish may have any value, for example, about 10 cm. Plural seeds may be placed in each chamber 406 if desired.

Figure 5:
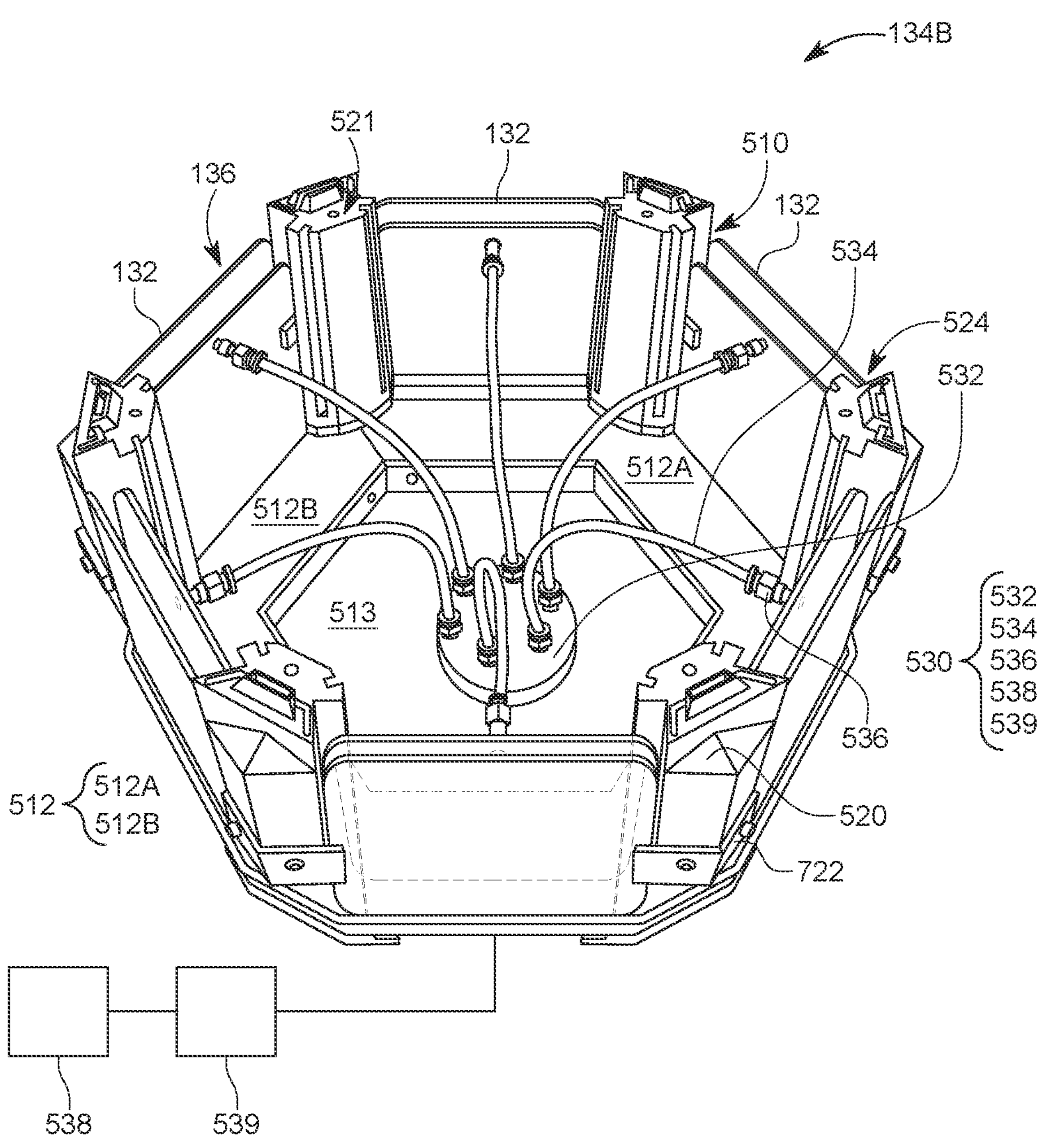
FIG. 5 illustrates a stage of the carousel having plural petri dishes and each petri dish being configured to be supplied with water by an irrigation system.
Figure 6:
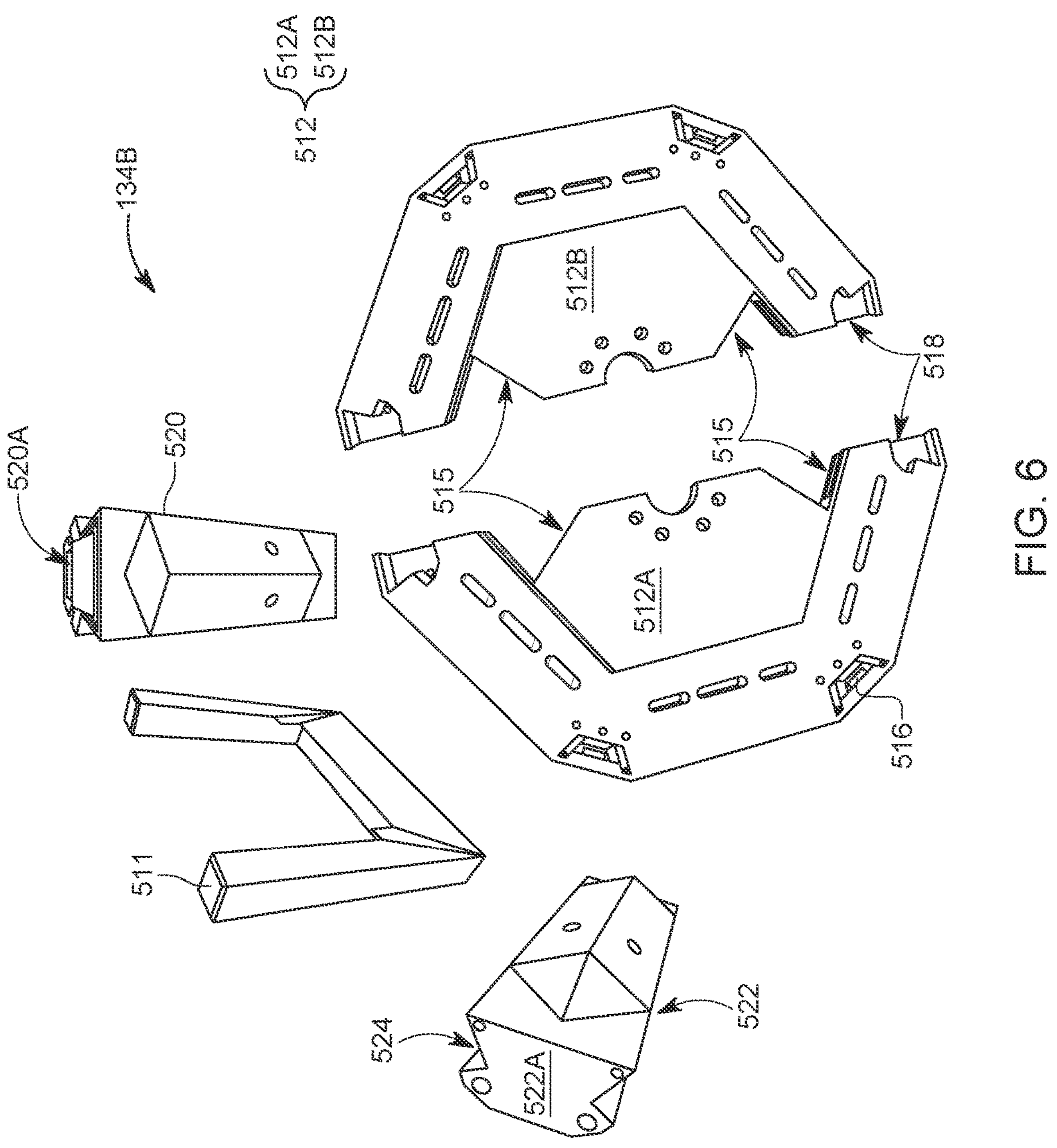
FIG. 6 shows the modular structure of each stage and the various components that are used to build the stage.
Figure 7:
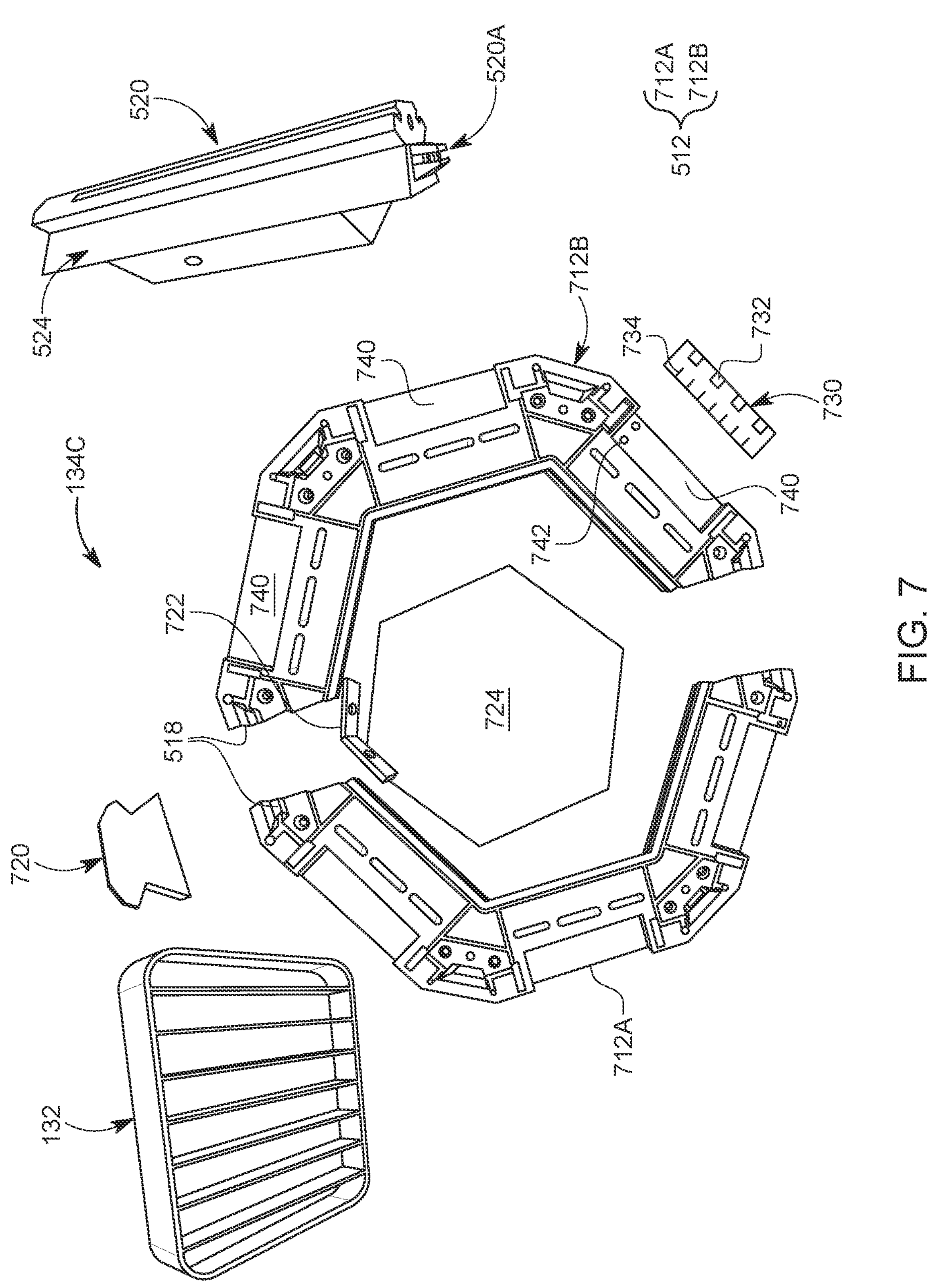
FIG. 7 shows the modular structure of another stage and the various components that are used to build the stage.

The dimensions of the petri dish 132 are selected to fit a corresponding slot 510 in a stage 134B of the carousel 134, as shown in FIG. 5. FIG. 5 shows the middle stage 134B having 6 slots 510, each one holding a corresponding petri dish 132. The middle stage 134B is made of a base frame 512 formed from two halves 512A and 512B, which can be attached together with screws or brackets (not shown). FIG. 5 also shows the base frame 512 having a bottom 513. The two halves 512A and 512B may be 3D printed in separate sections or monolithically so that when assembled, one or more openings 515 are formed in the bottom of the base frame 512, as shown in FIG. 6. Different halves 712A and 712B are shown in FIG. 7 and they also form a base frame 512. The different halves shown in FIGS. 6 and 7 may be used for different stages of the carousel. In one application, either the halves of FIG. 6 or the halves of FIG. 7 are used to make the entire carousel.

The two halves shown in FIG. 6 may have depressions or cavities 516, formed along a periphery of the base frame, which are shaped to mate with corresponding ridges 520A formed in columns 520. The columns 520 are added to the base frame 512, either by using screws, glue, magnetic implants, or other similar methods, to form a support structure for the next stage and a holding structure for the petri dishes 132. The slots 510 illustrated in FIG. 5 may be formed either with brackets 511, which are attached to two adjacent columns 520, as schematically suggested by FIG. 6, or may be formed directly by the columns 520. Note that FIG. 6 shows one column 522 having a flat end 522A, and this column may be used for joining the two halves 512A and 512B, i.e., for fitting the flat end 522A into a combined depression 518 to be formed when the two halves 512A and 512B are joined together. All the elements in FIGS. 6 and 7 may be 3D printed for reducing the cost of the system. In one application, when the slots 510 are defined by the columns 520, the petri dishes 132 may be shaped to directly fit into slots (or shoulders) 524 formed in the columns 520/522.

Depending on the location of the stage, i.e., bottom or middle or top stage, the configuration of stages can be slightly different. For example, FIG. 7 shows a top or middle stage 134B/134C, made of the two halves 712A and 712B, but different from the two halves 512A and 512B of the previously discussed shape, which is used for the bottom stage 134A. These two halves 712A and 712B are connected together with a common piece 720 that fits into the combined depression 518. A bracket 722 may also be used to fix the two halves to each other. The bracket 722 may be sized to extend over the slot 510 to hold in place the petri dish 132, when placed in the slot, as visible in FIG. 5. A bottom plate 724 may be fitted between the two halves 712A and 712B to close this stage. FIG. 7 also shows one of the petri dishes 132 (the transparent face 412 that is closing the petri dish is missing) that will be hosted between two columns 520. Note that these 3D parts may be mixed as required with the corresponding parts from the other stages.

In one embodiment, one or more of the stages are provided with an irrigation system 530, as shown in FIG. 5. The irrigation system 530 includes a manifold 532, which is placed on the bottom plate 513. The manifold 532 receives at an inlet (not shown) water and splits this water into six different flows, to be fed to the six different petri dishes 132 in the current stage. Corresponding conduits 534 are connected to the output of the manifold 532. Each conduit 534 is also connected to a petri dish input 536, which is attached to the back wall of the petri dish 132, and fluidly communicates with the chamber 406 of the petri dish, to directly provide the water to the soil media. FIG. 5 also shows the bracket 722 being attached to the column 520 and holding the petri dish 132 against the shoulder 524. With this system, each petri dish in a stage of the carousel can be irrigated equally according to the needs of the plants. To ensure uniform water distribution among the plural petri dishes for a given stage, in one embodiment, each petri dish input 536 or conduit 534 has a nozzle (not shown) with a narrow cross-section (like a needle) for providing resistance to the incoming water, so that the combined resistance provided by all the nozzles creates a pressure in the fluid that uniformly distributes the water from the manifold 532. The irrigation system 530 may further include a water reservoir 538, located next to the system 100, and a pump 539 for pumping the water from the reservoir 538 to the manifold 532. The pump 539 may be controlled by the control subsystem 160. The reservoir 538 may hold not only water, but any other liquid desired to be supplied to the plants, for example, plant nutrients, chemical compounds, hormones, etc.

FIG. 5 further shows that each column 520 may include a conduit 521 that extends through the entire length of the column. This conduit is used to provide electrical power and/or signals to upper stages. For example, in the embodiment shown in FIG. 7, a light element 730 is provided for each petri dish 132. Thus, each of the halves 712A and 712B is provided with corresponding slots 740 for receiving the light element 730. The light element 730 may have plural LED elements 732 and one or more electrical contacts 734 that engage with corresponding electrical contacts 742 (e.g., pogo pins or spring-loaded pins) in the slots 740. Thus, each light element 730 is configured to slide into the corresponding slot 740 and illuminate a corresponding petri dish. In one application, each light element 730 slides perpendicular to the vertical axis Z into the corresponding slot in the base frame. Each light element may have different LED elements so that any desired wavelength combination usable for a plant may be generated. The amount of light and the wavelength of the light supplied to the seeds may be controlled by the control subsystem 160. The power for the LED elements may be supplied by wires that extend through the conduits 521 in each column 520. In one application, the control subsystem 160 is capable to independently adjust each light element 730, i.e., provide the desired wavelengths and intensities for all petri dishes.

Figure 8:
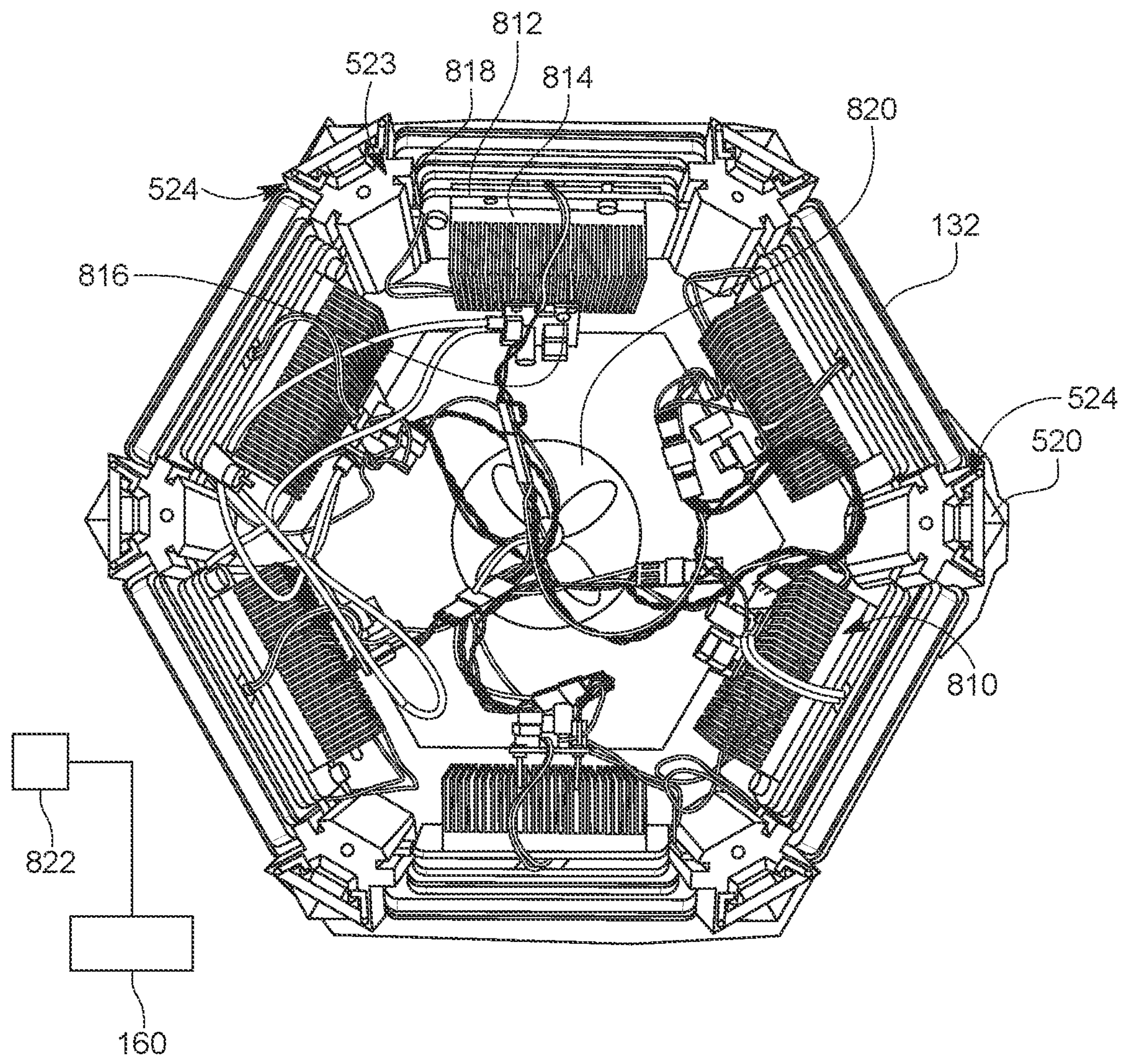
FIG. 8 shows another stage of the carousel having plural petri dishes and each petri dish being configured to have a temperature-controlled element for controlling a temperature of the soil within the petri dish.

In another embodiment, which may be combined with any of the previous embodiments, each petri dish 132 is supplied with a temperature-controlled element 810, as shown in FIG. 8. The temperature-controlled element 810 may be a Peltier element that is capable to cool or heat, depending on the polarity and magnitude of received current. The Peltier elements are connected to the control subsystem 160 via communication cable for being supplied with a corresponding temperature setting command. The processor of the control subsystem 160 is configured to turn on and off or regulate the Peltier elements according to a given schedule to achieve a desired temperature. The temperature-controlled element 810 may have a main body 812, which includes the semiconductor material that generates the heat. A radiator or a heatsink 814 may be attached to one side of the body. The body 812 may be placed with one side directly in contact with the petri dish 132. The radiator 814 may be placed inside the chamber of the stage 134C. A local controller 816 may be placed on the radiator. The body 812 may have small wings 818 that are sized to slide into corresponding channels 523 formed into the column 520 so that the temperature-controlled element can be removably attached to each petri dish in a given stage. Note that the channels 523 formed in each column 520 are in addition to the slots or shoulders 524, as illustrated in FIG. 8. Because of the wings 818, the temperature-controlled element 810 may be quickly slided out and in for a given petri dish as desired. The figure also shows the wiring associated with the temperature-controlled elements 810. In one embodiment, it is possible to provide a fan 820 in the top capping plate of the final stage to remove the heat generated by the temperature-controlled elements, if so desired. In this way, the fan is capable to expel the hot air from the entire carousel by creating negative pressure inside, which draws ambient air through the bottom stage. One skilled in the art would understand that the fan may be placed in other locations, for example, in the bottom or a middle stage of the carousel if so desired. All these elements may be controlled by the control subsystem 160. In yet another embodiment, an external temperature sensor 822 may be placed outside the system 100, for monitoring an ambient temperature. The control subsystem 160 can receive the temperature recorded by the sensor 822 and may adjust the temperature of the temperature-controlled elements 810 to be at a given temperature above or below the room temperature, as desired by the operator of the system.

Figure 9A:
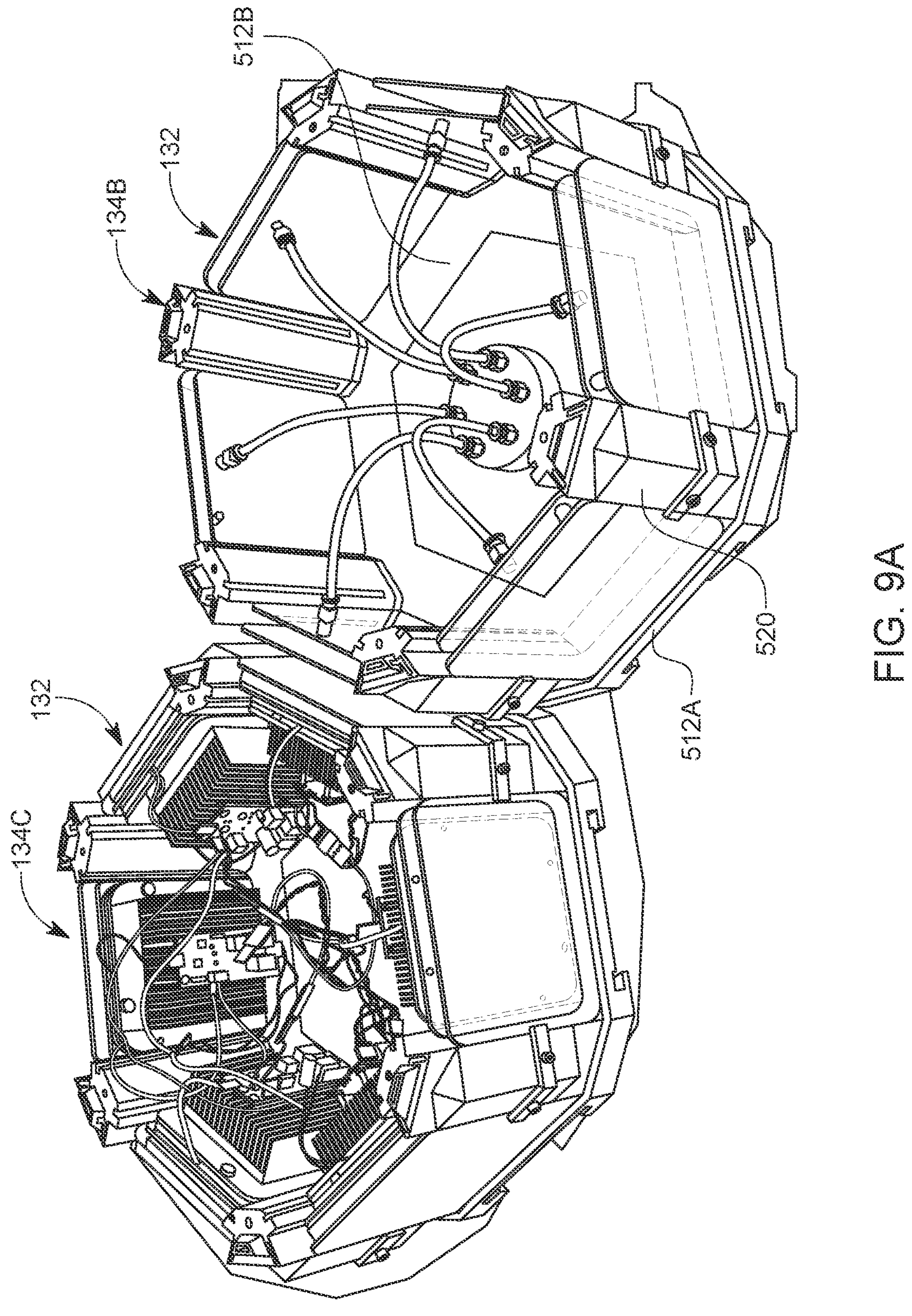
FIG. 9A shows two stages, one having an irrigation system and one having temperature-controlled elements.
Figure 9B:
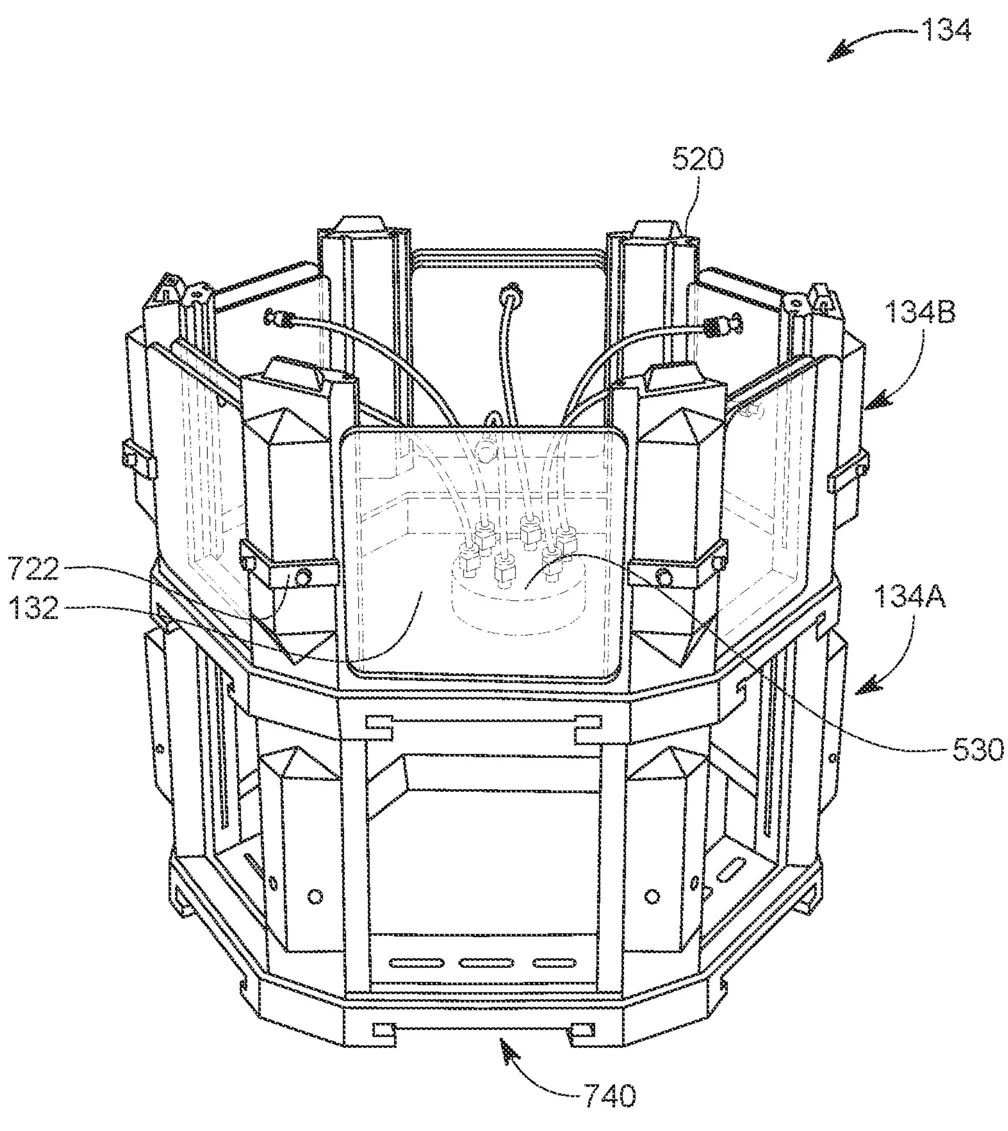
FIG. 9B shows the two stages being stacked up on top of each other.

FIG. 9A shows two stages 134B and 134C placed next to each other. It is noted that in this embodiment, the stage 134B has the irrigation system 530 while the stage 134C has the temperature-controlled elements 810. These systems may be easily swapped if so desired. As shown in FIG. 1, these stages are stacked on top of each other. FIG. 9B illustrates two stages 134A and 134B placed on top of each other to form the carousel 134.

Figure 9C:
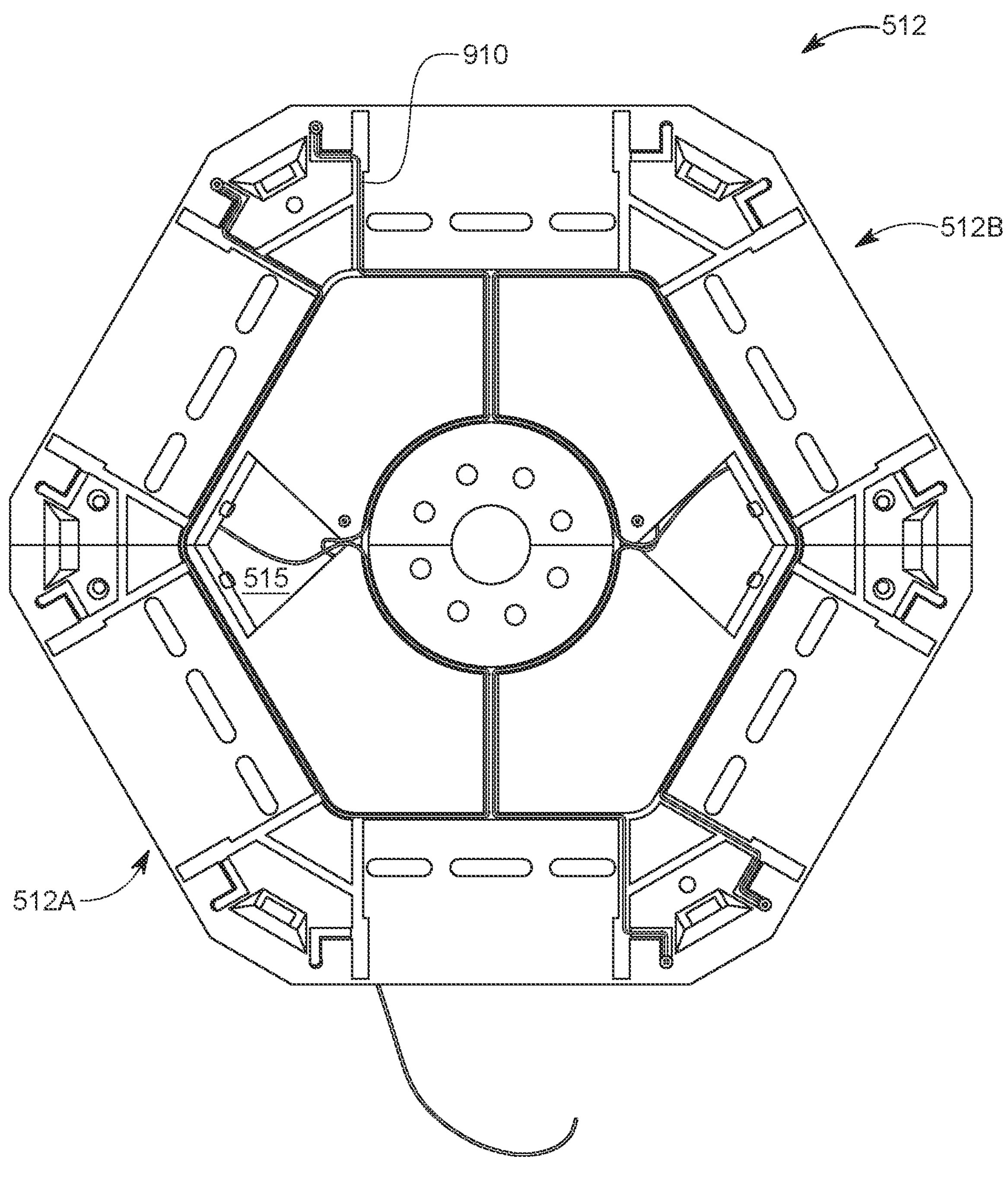
FIG. 9C shows the wiring of a base of a first stage.
Figure 9D:
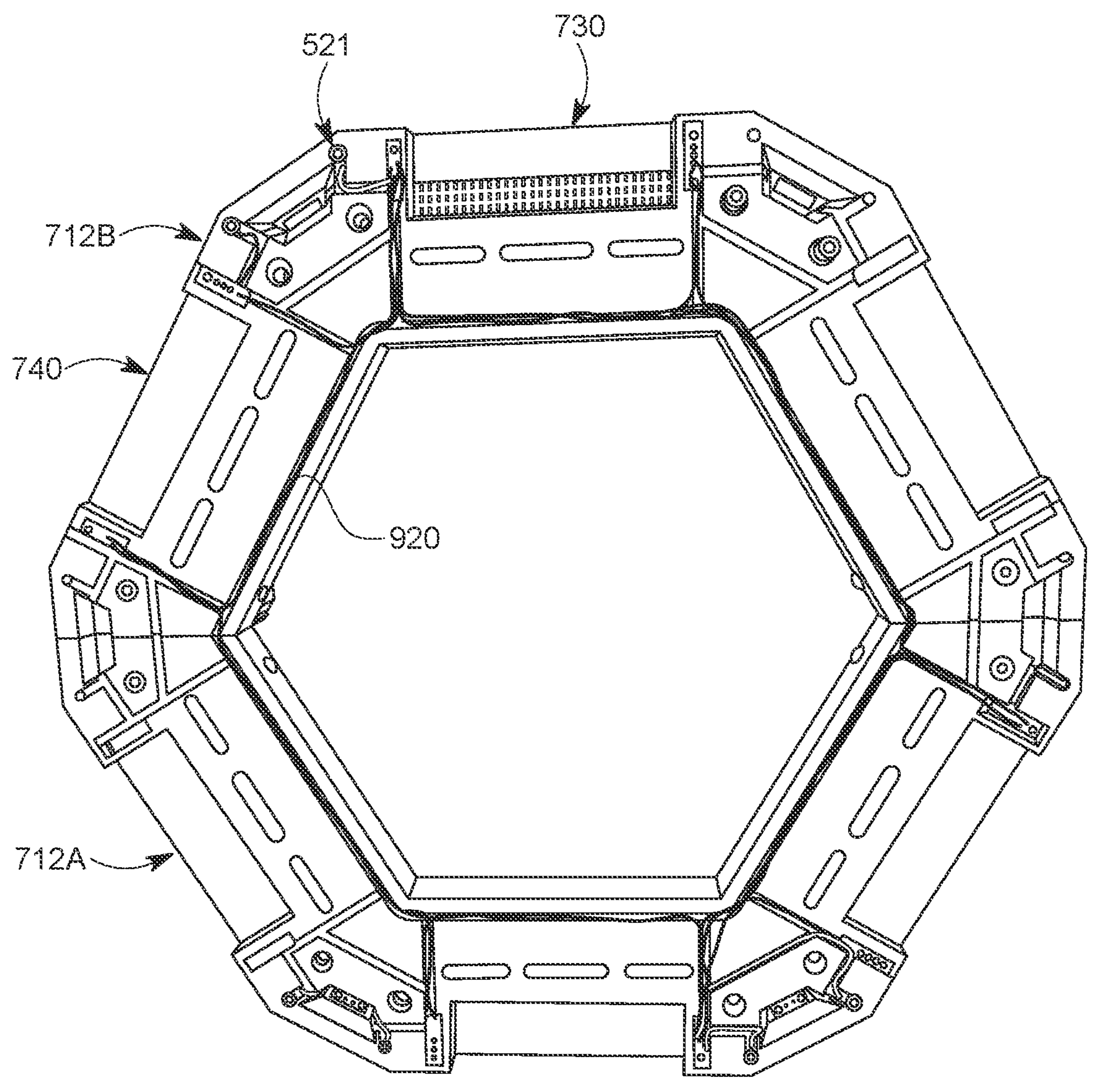
FIG. 9D shows the wiring of a base of a second stage of the carousel.

As discussed above, there is a first wiring for the light elements 730 and a second wiring for the temperature-controlled elements 810. The first wiring 910 is illustrated in FIG. 9C, with the individual wired being inserted into corresponding grooves into the base frame 512. Note that the wires 910 extend between the positions of the columns 520 and then go through the openings 515 outside the carousel, to the power source 210. A different base frame 512, which is used for an upper stage is shown in FIG. 9D, and this figure shows the second wiring 920 for the light elements 730. The second wiring 920 may also be provided through slots formed in the base and through the electrical conduit 521 formed in the column 520. Note that each column may have more than one electrical conduit 521, so that the first wiring 910 is not in contact with the second wiring 920 if the two wirings are provided in the same column. In one application, it is possible to use a first subset of the columns 520 for the first wiring 910 and a second subset of the columns 520, which is different from the first subset, for the second wiring 920. In yet another application, the wiring for the heating elements is not provided through the columns 520.

Note that each stage of the carousel 134 can be assembled from the corresponding halves of the base frame and six columns after which six petri dishes are placed in corresponding slots. Next, either an irrigation system or temperature-controlled elements are added to corresponding petri dishes. Then, a next stage is assembled and added at the top or bottom of the existing stage. This operation is continued until the final carousel is obtained. The wiring of the temperature-controlled elements is directed through corresponding holes formed into the bottom plate of each stage while the water conduits from the irrigation system are attached to the corresponding ports of the petri dishes. Light elements are slid into the base frame, above each petri dish to provide the desired wavelength. For assembling the entire carousel, one only needs to connect the various pieces shown in FIGS. 6 and 7 to each other, either with screws, glue, or magnetic inserts, similar to a Lego type game. Thus, the carousel 134 is easily assembled or disassembled, which makes it highly portable. Further, the carousel can be configured, depending on the desired seed investigation, to have more or less stages, to have or not an irrigation system, to have or not a temperature-controlled element, etc.

The control subsystem 160 includes a processor and memory and the processor is configured to control the actuation sub-systems, the camera, and the carousel so that continuous images are taken of the seeds/plants in each petri dish. The processor is also configured to control the irrigation system, the temperature-controlled elements, and the light elements. Various schedules for all the heating/cooling elements may be stored in the memory and the processor is configured to run these schedules for each individual heating/cooling element. Furthermore, various schedules for all the lighting elements may also be stored in the memory and the processor is configured to run these schedules for all lighting elements. The operator of the MultipleXLab system 100 interacts through an interface with the control subsystem 160 to input the desired temperatures, light composition and intensity, and amount of liquid to be delivered to each petri dish. The times when these parameters need to be changed may also be stored in the memory so that the processor activates the corresponding subsystem at the desired time. For example, the operator of the system 100 may desire to have each petri dish imaged every 10 minutes. The processor is configured to calculate how often the carousel 134 needs to be rotated and the camera to be moved along the Z axis to achieve this goal. In one application, the operator may instruct the processor to obtain higher resolution images for certain chambers 406 of the petri dish. For this capability, the processor instructs the actuator of the camera to move it along the X axis and also instructs the actuator of the carousel to move it along the Y direction to better focus the camera on the desired chamber. Any desired level of actuation can be programmed into the control subsystem 160.

In addition, the control subsystem 160 may be configured to implement an image segmentation pipeline powered by machine learning to facilitate and speed up the analysis of the large number of images acquired by the imaging subsystem 110. In another application, a different computer or server does the image segmentation and the control subsystem 160 may communicate with this computer or server. This approach provides an attractive solution for fast detection and measurement tasks in complex applications, providing a basis for automatic measurement of phenotypic traits. This implementation can perform supervised and non-supervised root segmentation using Convolutional Neural Networks (CNNs), which works based on classical deep-learning architectures. These new solutions are useful for automating data extraction of large datasets, such as those generated when using the carousel. In agravitropic roots, high temporal resolution of image acquisition can provide the basis for tightly expansion of the bounding boxes around roots following every successive hour, which allows the system to compute the root pixels inside each bounding box even when discontinuation of root components may take place during development due to several reason, such as obstruction of roots onto itself, or by the hypocotyl, seed coat or cotyledons. The system is configured with functional-structural modeling to evaluate root-phenotypic metrics quantitatively aggregating multiple phenes.

Thus, the MultipleXLab system can be used in multiple applications like: i) screening for particular phenotypes resulting from ethyl methanesulfonate (EMS) screens including germination rates, root length, and gravitropism; ii) assessing mutants' response to multiple stresses such as salinity and nutrient deficiency; and iii) monitoring growth response to growth-promoting substances and beneficial bacteria, or resistance to pathogens. The system can also be implemented to study the growth dynamics and dissect differences not only between mutants but also seed batches.

Figure 10:
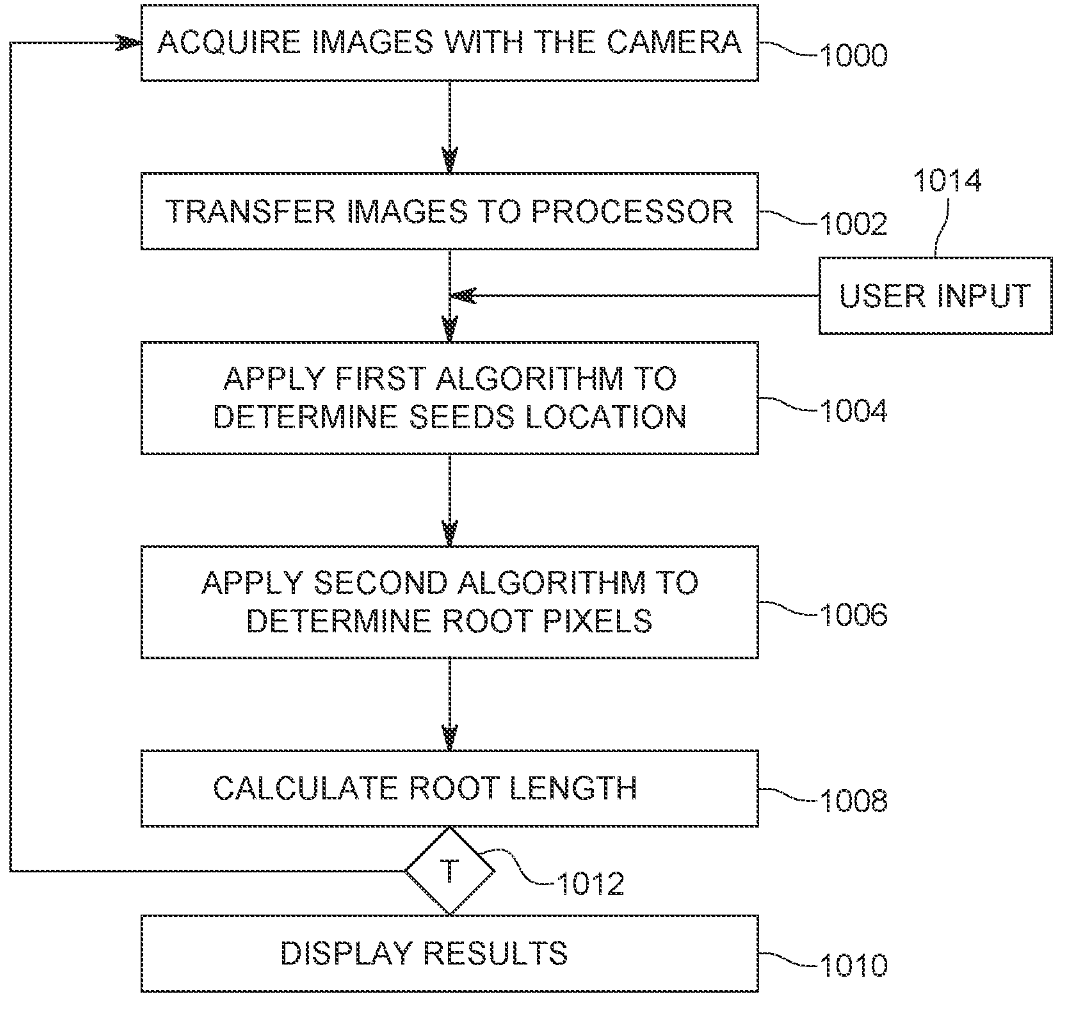
FIG. 10 is a flow chart of a method for analyzing acquired images of the seeds located in the petri dishes.

An example of a possible implementation of the image segmentation pipeline is now discussed with regard to FIG. 10. For this embodiment, to automate image acquisition and facilitate stacking to increase the system potential, the imaging subsystem 110 was micropositioned with the aid of stepper motors capable of reaching a maximum resolution of 1 μm per step, which facilitates refocusing and acquiring z-stacks to mitigate the downsides of a shallow depth-of-field (DOF) in extreme macrophotography. This feature enables the end user to maximize the optical resolution of the imaging system by increasing the numerical aperture of the lens to its optimal maximum. This maximization results in shallow DOF images that can be automatically stacked and systematically masked using computer software and post-processing workflows, producing an overall sharper image with an extended DOF.

In this embodiment, the system 100 was configured to capture dynamic biological processes in challenging environments using the optical arrangement and resolution discussed above. To this end, the time-lapse imaging of the plant samples was set up using the camera's built-in intervalometer, to establish an adequate frequency for visualizing dynamic processes. This setup allowed to autonomously operate the camera in step 1000 and use the processor to control the system for more specific and intricate tasks, such as automated focus stacking operations.

Figure 11A:
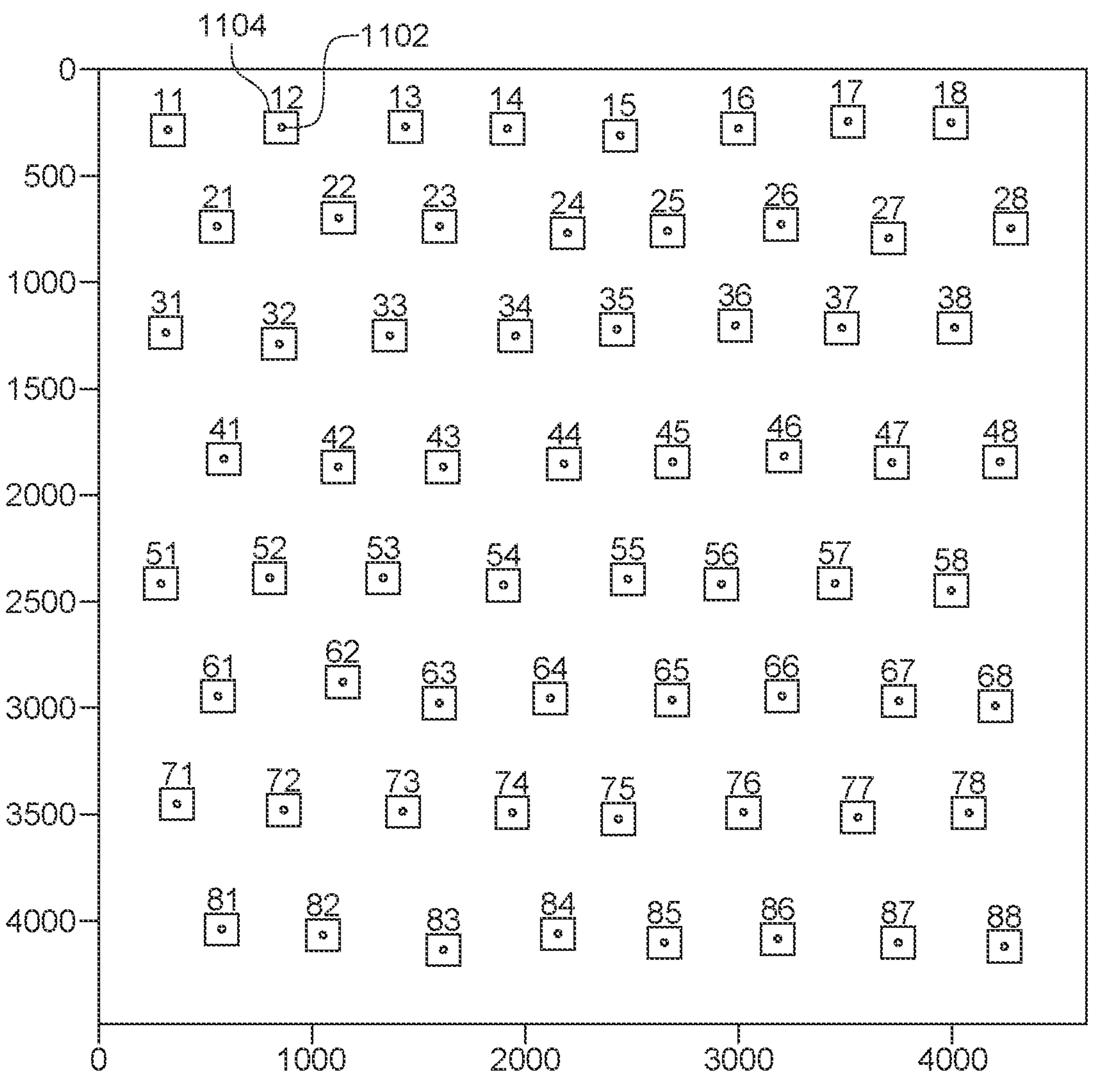
FIGS. 11A and 11B illustrate a graphical output of the method for analyzing the acquired images, with FIG. 11A showing the location of the seeds in the petri dishes and FIG. 11B illustrating the roots of the seeds.
Figure 11B:
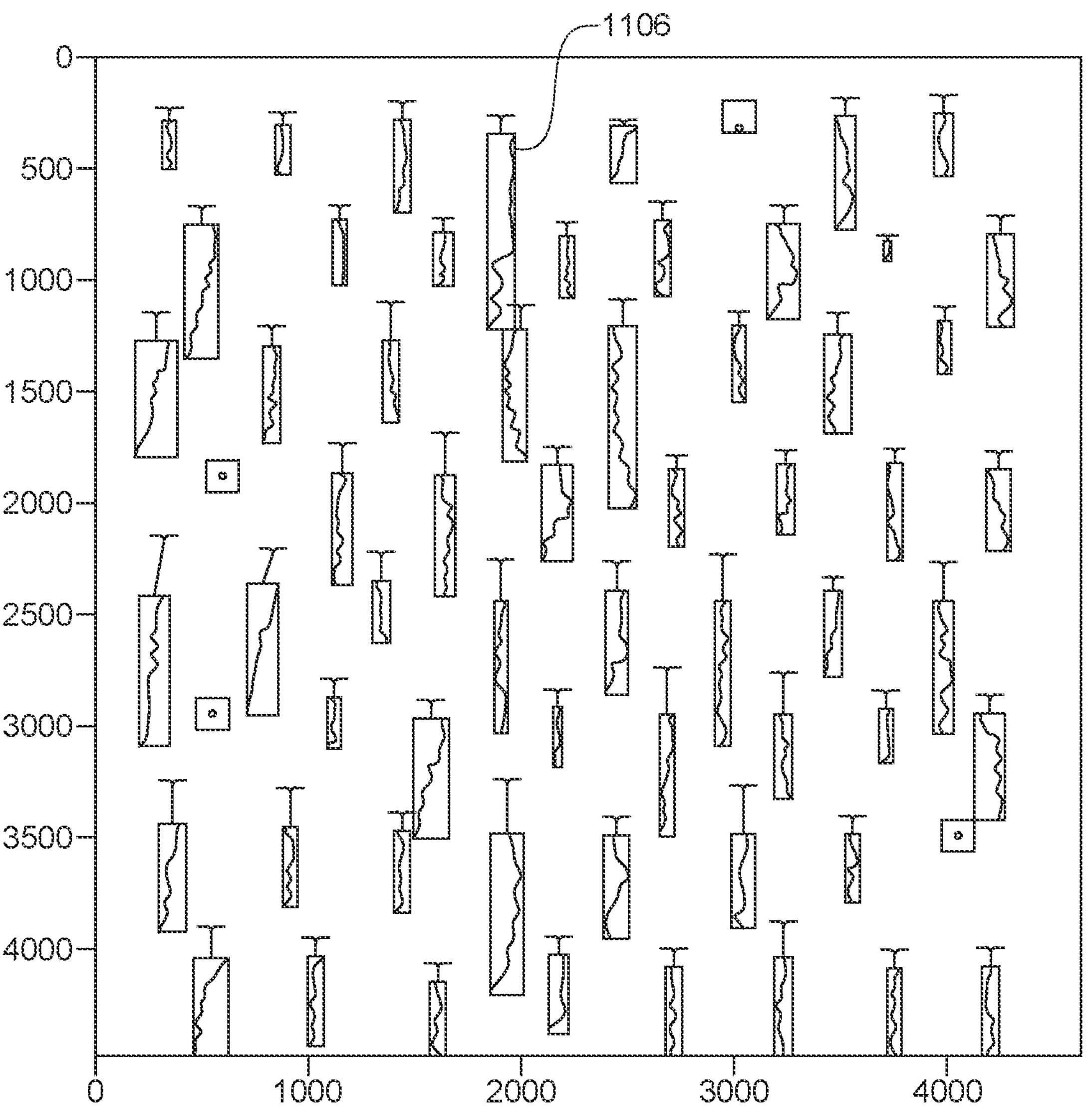
Figure 11C:
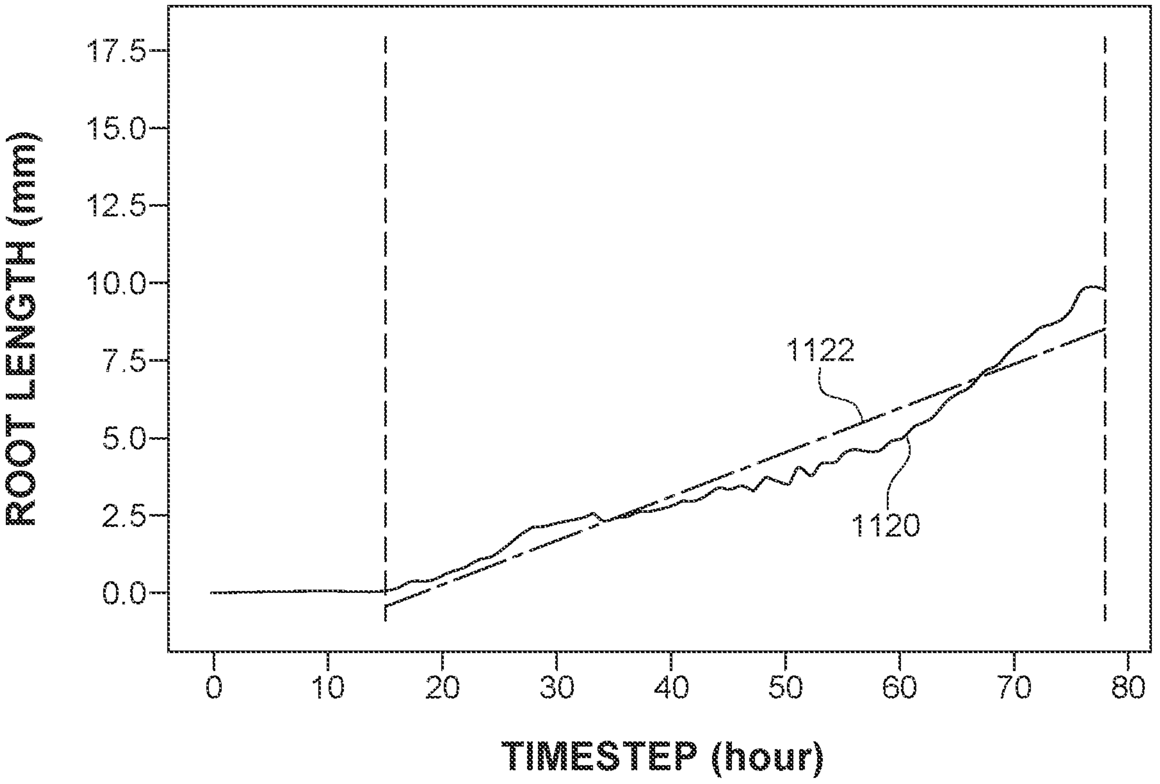
FIG. 11C illustrates the graph used by the system for estimating the root lengths of the seeds.

Because plant roots grow underground, noninvasively monitoring their changes in time and space is challenging. To overcome this challenge, the transparent petri dish was used. Note that the petri dish may have a small thickness, for example, 1 cm or less, and thus it is very likely that the roots are visible in the chambers 406. The camera 112 imaged the roots for a couple of days. The system automatically exports in step 1002 the acquired temporal information as a graphical germination dashboard (see FIGS. 11A and 11B) accompanied by a datasheet file containing all data throughout the growth cycle, from the imaging subsystem to the processing subsystem. The developed image processing pipeline platform, which combines traditional computer-vision algorithms with deep learning, was used to evaluate the roots growth. The image processing pipeline platform splits the large images (e.g., 4639×4480) into patches of 256×256 pixels, resizes the 256×256 patches to 32×32, gets predictions from each patch, and then stitches together the predicted patches to create a pixel-wise mask of the large image. In one application, the U-Net convolutional neural network was used to predict each patch. More specifically, the process follows a semantic segmentation of the last frame, then performs an instance segmentation, applies a feature extraction algorithm to detect the edge of the root, and then uses a linear regression for calculating the length of the root. These steps are then repeated for all instances in the timelapse. At its core, the pipeline platform relies on two deep learning models for image segmentation: SeedNet for finding seed pixels in step 1004 and RootNet for finding root pixels 1102 in step 1006. The pipeline platform starts by analyzing the first frame 1104 and finds the seed pixels using the SeedNet model in step 1004. The pipeline uses the OpenCV connected component algorithm to locate the individual seeds shown in FIG. 11A. The connected components analysis returns the bounding boxes 1106 for each seed instance. The pipeline platform further employs RootNet (a deep learning model) in step 1006 to locate the root pixels in each frame and expands the bounding boxes 1106 as the roots grow, using the connected component algorithm. The pipeline platform determines the bounding boxes 1106 for each root in each frame as shown in FIG. 11B. Then, using the skeletonization algorithm implemented in the scikit-image processing library, the pipeline platform calculates in step 1008 the root length L of each plant across the time series, and visualizes it in step 1010, as shown in FIG. 11C. After the root length versus time was plotted for each plant in a growth cycle (see curve 1120 in the figure), a line 1122 was fitted to the plot section in step 1010, starting with the germination and ending with either an overlap between neighboring roots or the termination of the time series. Then, the processor calculated the growth rate of the selected seed as the slope of the fitted line 1022. Note that the method may have an optional step 1012 to determine, after calculating the roots' lengths in step 1008, whether a timer has elapsed, and if not, the process returns to step 1000 and continues to collect more images and to recalculate the roots' lengths as the plants are continuously growing.

In one application, the image files that are transferred in step 1002 are edited as a batch to even out the brightness throughout the images. The pipeline platform then scans all these files with QR codes and relocate them. The renamed files carrying the mutant's names (plus metadata info) are relocated to specific folders and loaded into the segmentation pipeline, which performs micro-alignment of frames and cropping of the central part of the image (assigned by the user) with just the seeds and dark or contrasty media, and then these images are imported into the segmentation pipeline workflow for processing in step 1004. In one application, the user inputs an optional step 1014 a root folder, where all images are located, scale information, and seeds to be chosen from frame 1.

In this regard, the method illustrated in FIG. 10 starts by finding the seed locations from the first frame. Another deep learning model called SeedNet is used to find the seeds.

For step 1006, the bounding boxes need to be determined to measure the length of each root. The algorithm used in this step combines the initial seed locations with the algorithm called "connected components," which is known in the art and thus, its description is omitted herein. For this step, the method finds all connected components from pixel mask using the connected components algorithm. Ideally, there should be one component per bounding box, but there might be multiple ones. All components inside one bounding box will be considered to be a single entity. The algorithm checks if there are any of those components outside the bounding box. If there are component(s) that extend outside the bounding box, then the algorithm fits a new tight bounding box. Then, the algorithm moves to the next pixel mask and repeats the sub-steps noted above until the results shown in FIG. 11B are obtained. Having the pixel masks and the bounding boxes per frame, the method measures in step 1008 the length of the root. The length will be measured using area and circumference of the root within a bounding box. For this purpose, a linear regression model may be used.

The above discussed method has been tested with the MultipleXLab system 100 for wild-type Arabidopsis seeds. The F1 scores (harmonic mean of precision and sensitivity) for SeedNet and RootNet on the test set were 0.8048 and 0.7395, respectively. The mean absolute percentage error on the root length measurements using long wildtype (WT) roots for validation was 4.18% (N=12).

To test the potential of MultipleXLab system 100, the seed germination and root outgrowth was monitored for several developmental, auxin transport and cell-cycle mutants. For the root-developmental mutants, the stem cells and asymmetric cell division factors scarecrow (scr), shortroot (shr), Retinoblastoma related 1 (RBR1) RNA interference (Rbi), and jackdaw (jkd) were used; the quiescent center function regulator Wuschel-related Homeobox 5 (wox5); and the root hair patterning double mutant triptychon caprice (trycpc). It was found that WT plants have a germination index ranging between 92 and 100%, as shown in Tables 1 to 4 in FIGS. 12A to 12D, respectively. The letters a to d in these tables indicate that individual means are significantly different ($p<0.5$). Among these mutants, only shr and trycpc exhibited a lower germination index of 74% and 80%, respectively, as seen in Tables 1 and 2.

Next, the auxin transport mutants were tested using the auxin influx carriers aux1 and lax3, the auxin efflux carrier pin2, and the double mutant pin2aux1. It was found that lax3 had a lower germination index (53%) compared to WT (92%) and other auxin transport mutants, as noted in Table 3.

The cell-cycle regulators e2fa-1, the cell-cycle-dependent kinase double mutants cdkb1;1cdkb1;2, and a mutant of the Arabidopsis D-Type Cyclin CYCD2;1 the cyclin d2;1 (cycd2-1) were also studied. It was found that e2fa-1 and cyclin d2;1 had a lower germination index than the WT at 78% and 80%, respectively, whereas other cell-cycle mutants were similar to the WT, as shown in Table 4.

Next, the growth rates were calculated by monitoring the germination and root growth of individual seeds and roots hourly for each mutant, based on the method illustrated in FIG. 10. Time-lapse imaging received from the camera 112 were combined with image segmentation based on deep learning in root systems. This approach allowed to simultaneously evaluate and extract differences in growth dynamics of thousands of samples and precisely detect the germination initiation timepoint. It was found that shr mutants have a slower growth rate, with an average growth rate (AGR) of 0.03135 mm/h in shr compared to 0.15672 mm/h in the WT.

Hourly image acquisition allowed the inventors to evaluate the growth rate of each mutant. It was found that the WT had the most significant growth rate during the initial 48 h (AGR=0.15672 mm/h for the entire cycle), while scr and Rbi grew more slowly (AGR=0.1324 and 0.11503 mm/h, respectively) in the beginning and caught up after 65 h, exhibiting growth rates similar to WT at the end. In addition, the shr mutants displayed a slow and constant growth (AGR=0.03135 mm/h) with the lowest growth rate of all the mutants. Despite not displaying statistically different root length phenotypes compared to the WT, the inventors found that the double mutant trycpc had a relatively constant growth rate during the first 30 h and was revealed to be slower throughout the entire cycle (AGR=0.14568 mm/h). In contrast, the wox5 growth was slow (AGR=0.15751 mm/h) due to delayed germination, as the initial growth was observed 4 h after the WT. Finally, jkd also displayed a slight delay in growth during the first 5 h but gained speed to reach WT's growth rate at the end (AGR=0.13914 mm/h).

Next, the inventors used the system 100 to observe the growth of mutants involved in the auxin transport. These mutants are challenging to evaluate because of their agravitropic phenotype, causing the root to curl and obstruct certain parts under itself, leading to discontinuity and artifacts during measurements. Thus, these mutants may introduce a biased result for the root length measurements. The inventors used the skeletonization algorithm to measure the root segment summation length within the root domain prescribed by the bounding box to mitigate this challenge. It was found that lax3 has significantly shorter root growth than the WT (AGR=0.09149 and 0.11854 mm/h, respectively). The double mutant pin2aux1 was similar to lax3. The efflux carrier mutant roots were also evaluated and the inventors found that pin2 (AGR=0.08241 mm/h) has significantly shorter roots than the WT (AGR=0.11854 mm/h). The roots of pin2aux1 (AGR=0.07152 mm/h) double mutants exhibited a phenotype similar to pin2, indicating that pin2 is epistatic to aux1 in term of root growth. While analyzing the growth dynamics of the auxin mutants, it was noticed that the WT controls had a 7-h delay in growth. Moreover, pin2 had the fastest germination, whereas pin2aux1 and lax3 had the slowest growth rate of the tested auxin mutants.

The cell-cycle mutants displayed an interesting growth rate. The analysis revealed that e2fa-1 (AGR=0.1223 mm/h) has a slightly slower root-growth rate than the WT (AGR=0.14602 mm/h). It was also observed large fluctuations, especially during the early time points. For example, cycd2, 1 seemed to have a faster growth (AGR=0.16982 mm/h), which stabilized after 24 h, and cdkb1,1; cdkb1;2 (AGR=0.09782 mm/h) germinated faster. However, its growth halted and became slower until 15 h, after which the growth speed became similar to that of the WT (AGR=0.14602 mm/h). Finally, the e2fa-1 mutant behaves similarly to cdkb1,1; cdkb1;2 but resumed normal growth after 36 h.

These experiments indicate that the imaging system 100 discussed above provides a solution to the long-standing challenge faced by biologists when capturing images of dynamic processes in large samplings of living organisms. During growth, plant organs change continuously in shape and size and, particularly in the case of plants, are formed throughout an organism's entire life cycle. The system 100 was used to monitor the germination index and root-growth rate for thousands of Arabidopsis seeds. The ability of the system 100 to simultaneously image and quantify the growth rate of several samples in an hourly manner enabled the inventors to extract new phenotypes, such as the slower growth of Rbi and lax3 mutants and the faster growth rate for cdkb1, 1; cdkb1;2. The system can also dissect differences between mutants and evaluate the seed quality in different seed batches. The experiment using auxin mutants is a good example, where the delayed WT growth is most likely related to the seed batch.

The system 100 is also cheaper than the existing systems as it is based on cameras/lenses designated for the consumer market. After the above noted tests, the system was found to be more versatile than microscopes for simultaneously resolving macro- and micrometric structures, primarily due to its high-density pixel sensor and additional flexibility in lighting the specimens. Moreover, in the proposed system, the camera can be detached from the rail and repurposed for general photography. The various configurations proposed in this setup allow reasonable working distances between the outer-filter element on the lens and specimen, which permits proper illumination. Additionally, the optics can be easily stacked, and the widely available camera/lens mount adapters allow for fast and straightforward lens swaps, including infinity-corrected microscope objectives. These unique features allow the user of the system to alternate between a reduced FOV for maximum magnification or a larger FOV for optimized magnification, offering more flexibility to fit a wide range of specimen dimensions. In addition, this setup has the advantage of allowing the user to adapt inexpensive optics from innumerable different focal lengths, including the adapted legacy lenses, making this type of imaging system more versatile than most commercially established benchtop lab systems.

Figure 13A:
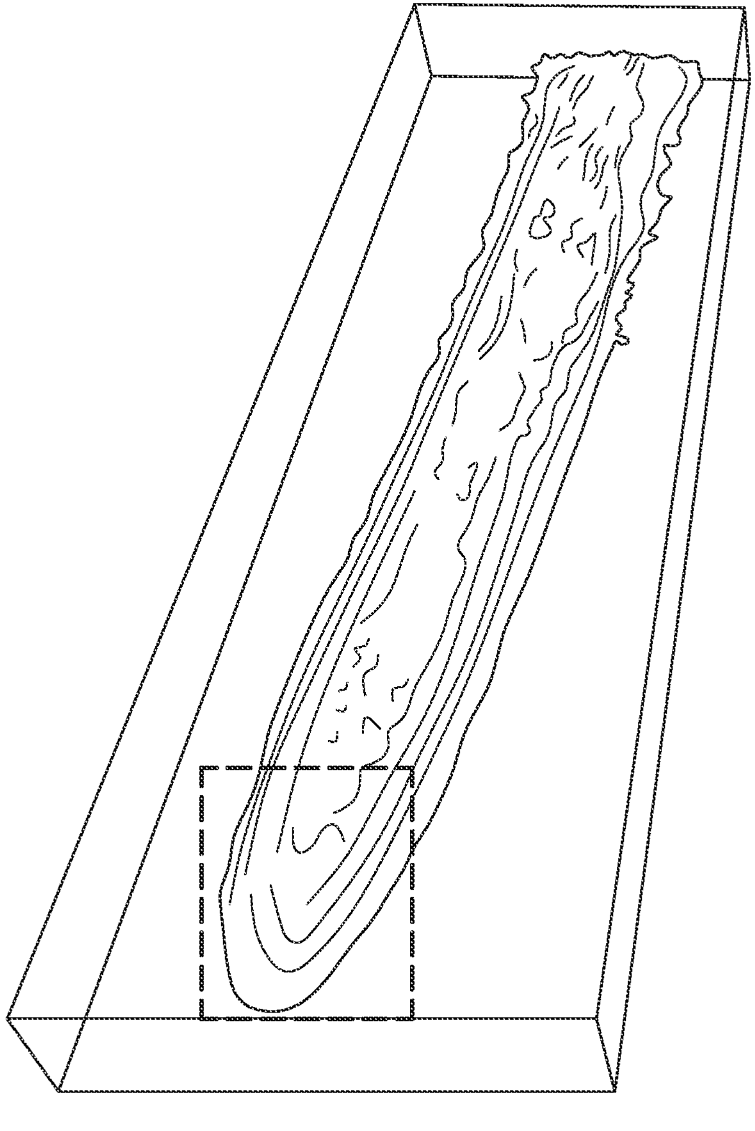
FIGS. 13A to 13C illustrate the constructed models for the roots of the seeds based on the acquired images.
Figure 13B:
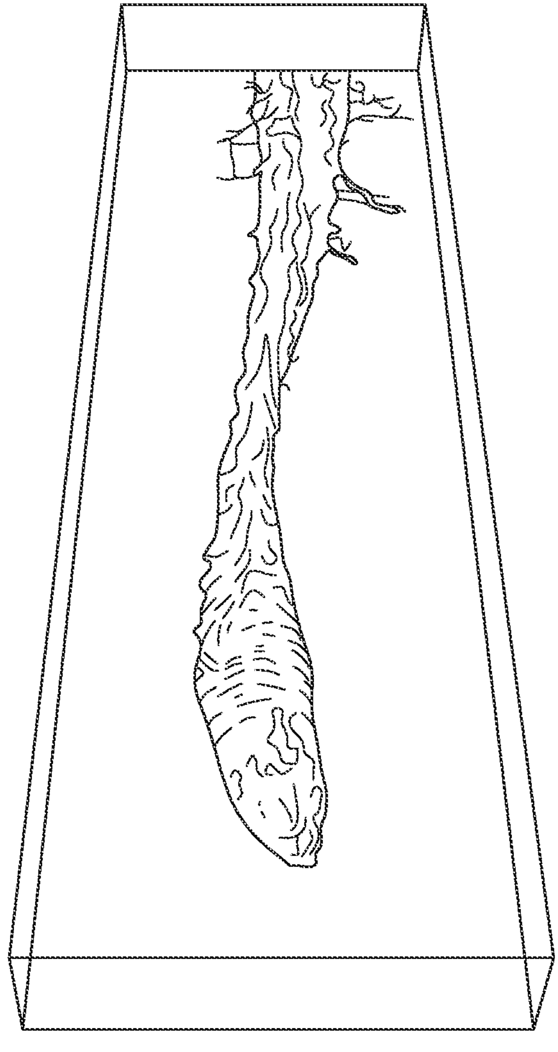
Figure 13C:
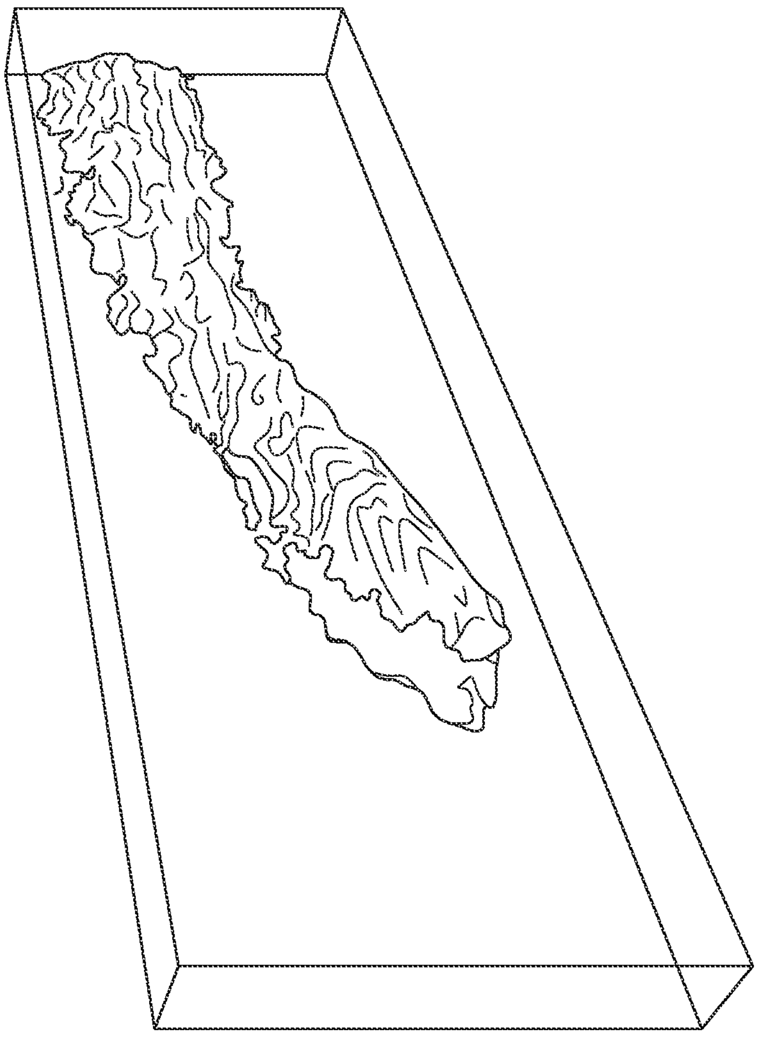

Creating surface topography images allows the proposed system to have unique applications, such as the nondestructive surface mapping of a living organism. This feature becomes relevant when dealing with living organisms subjected to changes in their surrounding environment (e.g., plant roots subjected to drought, nutrient depletion, and changes in soil composition) or reacting to continuous threats from pathogens, such as fungus, soil nematodes, and insect herbivores. Using this imaging setup, the inventors were able to monitor changes over time in the 3D structure of the root surface during drought, allowing to create a surface representation of the root topology for various conditions, e.g., FIG. 13A shows a hydrated root, FIG. 13B shows a dehydrated root, and FIG. 13C shows a rehydrated root. Combining the multiplate stage holder 134 with pre-programmed cycles enabled the inventors to continuously monitor and grow multiple specimens indoors and precisely control the lighting used for plant growth using a specific daily cycle (16 h on and 8 h off). The automation speed for acquiring multiscale images, stitching, and stacking makes the MultipleXLab system a versatile and powerful CNC microscope.

In addition, the inventors implemented an image segmentation pipeline powered by deep learning to facilitate and accelerate the analysis of numerous multidomain images. This capability of the system 100 performs supervised and unsupervised root segmentation using convolutional neural networks based on classical deep learning architectures. This new solution helps automate the data extracted from large datasets, such as those generated in the experiments discussed above. For example, in agravitropic roots, the hourly image acquisition of high temporal and spatial resolution provides a basis for tightly expanding bounding boxes around roots. This resolution allows the root pixels inside each bounding box to be computed even when root components may disappear during development, for example, due to an obstruction of roots into itself or by the hypocotyl, seed coat, or cotyledons.

High-throughput phenotyping technologies powered by artificial intelligence are important tools for advancing genetic gain in breeding programs and assessing the effects of natural variation or treatments on plant development. The system 100 demonstrates that computer-vision analysis permits autonomous image processing in pipelines designed to analyze gravitropism and explore temporal micro-morphometrics in overwhelmingly large multiscale datasets. These high-throughput analyses are necessary steps to alleviate bottlenecks in precision agriculture in crop phenomics. Some of these limitations are data storage and functional modes to evaluate root-phenotypic metrics with multiple and distinct traits quantitatively.

The system 100 is also small, which makes it portable. The carousel 134 can be easily removed from the carousel actuation subsystem 140 and from the support subsystem 150 and the imaging subsystem 110 may also be easily removed from its actuation subsystem 120. Thus, the entire system 100 can be quickly disassembled and reassembled at another location as necessary. The system is also modular, i.e., the carousel 134 can be assembled or disassembled as the needs dictate, more stages can be added or removed. Each stage may be quickly modified to have a lighting element, a heating element or an irrigation component. In addition, the camera 112 may be replaced with any other camera, making the overall system inexpensive and adaptive. The control subsystem 160 may be used together with the deep learning and computer vision algorithms makes the entire system to be able to automatically handle a large amount of collected data and to extract various features related to the seeds and roots planted in the petri dishes 132.

Figure 14:
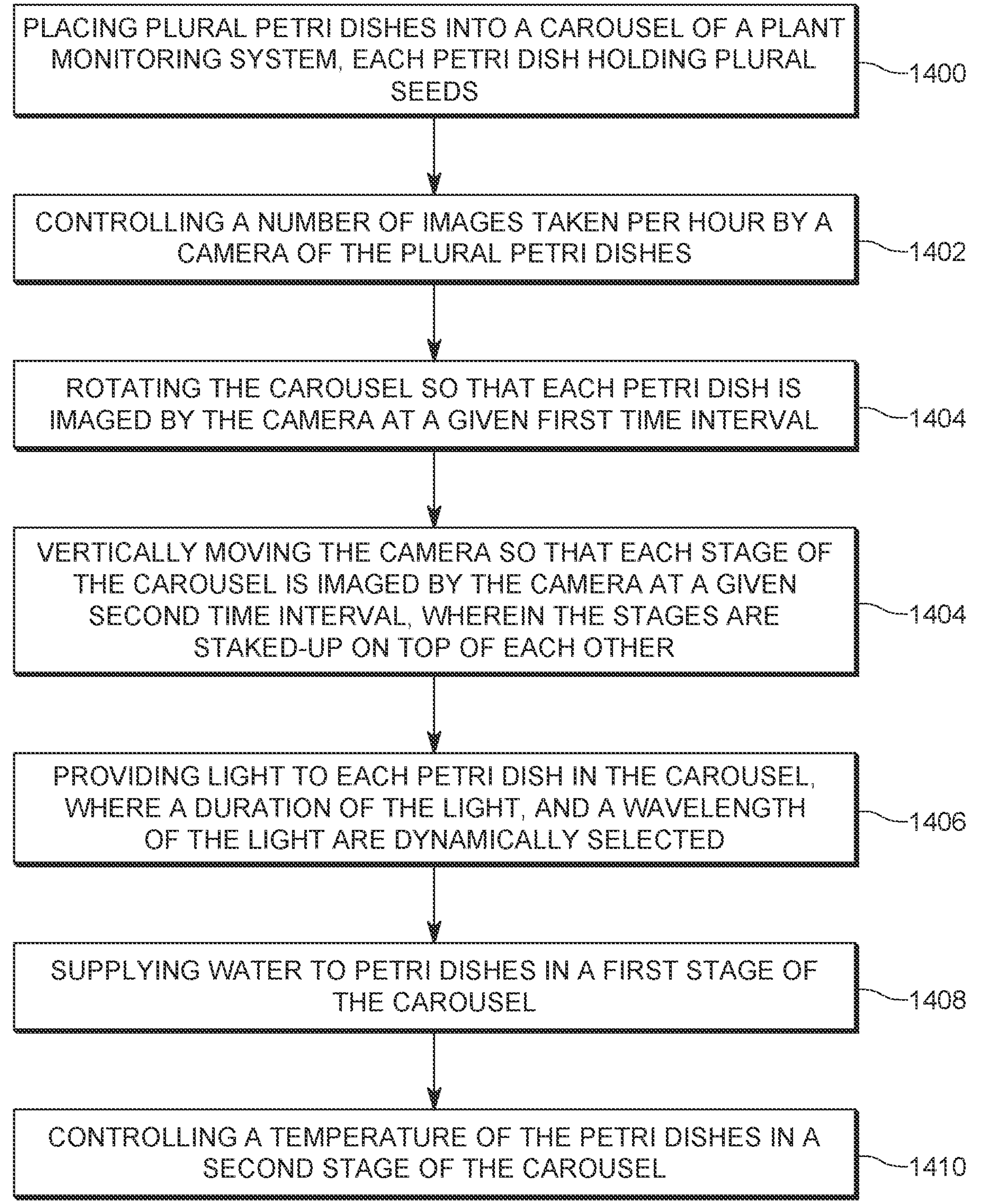
FIG. 14 is a flow chart of a method for controlling the carousel system for acquiring images of the seed growth.

A method for automatically monitoring plant grow with the system 100 is now discussed with regard to FIG. 14. The method includes a step 1400 of placing plural petri dishes into a carousel of a plant monitoring system 100, each petri dish holding plural seeds, a step 1402 of controlling a number of images taken by a camera per intervals specified by the user not exceeding a certain frequency, for example, every 10 minutes, a step 1404 of rotating the carousel so that each petri dish is imaged by the camera at a given first time interval, a step 1406 of vertically moving the camera so that each stage of the carousel is imaged by the camera at a given second time interval (for example, 10 minutes), where the stages are stacked up on top of each other, a step 1408 of providing light to each petri dish in the carousel, where a duration of the light, and a wavelength of the light are dynamically selected, a step 1410 of supplying liquid to petri dishes in a first stage of the carousel, and a step 1412 of controlling a temperature of the petri dishes in a second stage of the carousel. The method may further include a step of applying a first algorithm to the acquired images of the seeds to determine seed locations in the petri dishes, applying a second algorithm to the acquired images to determine pixels locations associated with roots of the seeds, and calculating the root length for each seed.

The disclosed embodiments provide a high-throughput, portable, modular, live-imaging root phenotyping system that uses deep learning and computer vision algorithms for automatically processing the collected images. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

The entire content of all the publications listed herein is incorporated by reference in this patent application.

[1] Zhao C, Zhang Y, Du J, Guo X, Wen W, Gu S, et al. Crop phenomics: current status and perspectives. Front Plant Sci. 2019; 10:714. https://doi.org/10.3389/fpls. 2019. 00714.

[2] Li D, Quan C, Song Z, Li X, Yu G, Li C, et al. High-Throughput Plant Pheno-typing Platform (HT3P) as a Novel Tool for Estimating Agronomic Traits from the Lab to the Field. Front Bioeng Biotechnol. 2020; 8:623705.

[3] https://plantphenotyping.com/products/plantscreen-sc-system.

[4] Nagel K A, Putz A, Gilmer F, Heinz K, Fischbach A, Pfeifer J, et al. GROWSCREEN-Rhizo is a novel phenotyping robot enabling simultaneous measurements of root and shoot growth for plants grown in soil-filled rhizotrons. Funct Plant Biol. 2012; 39 (11): 891-904.

[5] Jeudy C, Adrian M, Baussard C, Bernard C, Bernaud E, Bourion V, et al. RhizoTubes as a new tool for high throughput imaging of plant root development and architecture: test, comparison with pot grown plants and validation. Plant Methods. 2016; 12:31.

[6] Vadez V, Kholová J, Hummel G, Zhokhavets U, Gupta S K, Hash C T. LeasyScan: a novel concept combining 3D imaging and lysimetry for high-throughput phenotyping of traits controlling plant water budget. J Exp Bot. 2015; 66 (18): 5581-93.

[7] Granier C, Aguirrezabal L, Chenu K, Cookson S J, Dauzat M, Hamard P, et al. PHENOPSIS, an automated platform for reproducible phenotyping of plant responses to soil water deficit in Arabidopsis thaliana permitted the identification of an accession with low sensitivity to soil water deficit. New Phytol. 2006; 169 (3): 623-35. https://doi.org/10.1111/j.1469-8137.2005.01609. x.

[8] Clark R T, MacCurdy R B, Jung J K, Shaff J E, McCouch S R, Aneshansley D J, et al. Three-dimensional root phenotyping with a novel imaging and software platform. Plant Physiol. 2011; 156 (2): 455-65.

[9] Wu J, Wu Q, Pagès L, Yuan Y, Zhang X, Du M, et al. RhizoChamber-Monitor: A robotic platform and software enabling characterization of root growth. Plant Methods. 2018; 14 (1): 1-15. https://doi.org/10.1186/s13007-018-0316-5.

[10] Atkinson J A, Pound M P, Bennett M J, Wells D M. Uncovering the hidden half of plants using new advances in root phenotyping. Curr Opin Biotechnol. 2019; 55:1-8.

[11] Lien M R, Barker R J, Ye Z, Westphall M H, Gao R, Singh A, et al. A low-cost and open-source platform for automated imaging. Plant Methods. 2019; 15 (1): 1-14. https://doi.org/10.1186/s13007-019-0392-1.

[12] Bagley S A, Atkinson J A, Hunt H, Wilson M H, Pridmore T P, Wells D M. Low-Cost Automated Vectors and Modular Environmental Sensors for Plant Phenotyping. Sensors. 2020; 20 (11). https://www.mdpi.com/1424-8220/20/11/3319

What is claimed is:

1. A portable, modular plant monitoring system comprising:

an imaging subsystem configured to acquire images of plural plants with a camera;

an imaging actuation subsystem configured to support the imaging subsystem and to translate the imaging subsystem along a first horizontal axis X and along a vertical axis Z;

a carousel system having a carousel configured to hold the plural plants in plural petri dishes, wherein the carousel has a number of identical external, side faces;

a carousel actuation subsystem configured to support the carousel system, to translate the carousel along a second horizontal axis Y, which is perpendicular on the first horizontal axis X and the vertical axis Z, and to rotate the carousel about the vertical axis Z;

a support subsystem configured to hold the camera actuation subsystem and the carousel actuation subsystem; and a control subsystem configured to coordinate a movement of the camera along the first horizontal axis X and the vertical axis Z, a movement of the carousel along the second horizontal axis Y and a rotation about the vertical axis Z, image acquisition by the camera, and image processing to detect a characteristic of the plural plants.

2. The system of claim 1, wherein the carousel comprises:

plural stages stacked on top of each other, each stage of the plural stages being formed from a base frame, and plural columns (520) configured to be removably attached to the base frame.

3. The system of claim 2, further comprising:

the plural petri dishes, each configured to fit into a corresponding side face of the carousel, wherein a petri dish of the plural petri dishes removably fits into shoulders formed in corresponding columns.

4. The system of claim 3, wherein the petri dish has at least one face transparent to light.

5. The system of claim 2, further comprising:

a water manifold provided on the base frame and configured to distribute an incoming water flux to all petri dishes of a given stage via corresponding conduits, wherein each conduit is fluidly connected to an interior of a corresponding petri dish.

6. The system of claim 2, wherein the base frame has a slot corresponding to each petri dish to receive a light element.

7. The system of claim 6, further comprising:

plural light elements configured to be removably attached to the base frame with spring-loaded pins.

8. The system of claim 2, further comprising:

plural temperature-controlled elements configured to be attached to the plural petri dishes to control a temperature inside the plural petri dishes.

9. The system of claim 8, wherein each petri dish in a given stage has a corresponding temperature-controlled element.

10. The system of claim 1, wherein the control subsystem includes a processor that is configured to control (1) a number of images taken by the camera per hour, (2) a rotation of the carousel per hour so that each petri dish is imaged by the camera at a given first time interval, (3) a vertical movement of the camera so that each stage of the carousel is imaged by the camera at a given second time interval, (4) an amount of light that is supplied to each petri dish in the carousel for plant growth or imaging, (5) a duration of the light, and (6) a wavelength of the light supplied to each petri dish.

11. The system of claim 10, wherein the control subsystem is configured to:

apply a first algorithm to the acquired images of the plural plants to determine seed locations in the petri dishes;

apply a second algorithm to the acquired images to determine pixels locations associated with a root of the seed; and calculate the root length.

12. The system of claim 2, wherein at least one column of the plural columns has a conduit that extends through the entire column and is configured to carry an electrical wire.

13. A carousel system for holding seeds, the carousel system comprising:

plural petri dishes configured to hold the seeds; and a carousel having plural stages stacked on top of each other, each stage having plural external, side faces, and each external, side face being configured to hold a corresponding petri dish, wherein each stage includes, a base frame, and plural columns configured to be removably attached to the base frame and define slots to hold the petri dishes.

14. The carousel system of claim 13, further comprising:

a water manifold provided on the base frame of a given stage and configured to distribute an incoming water flux to all petri dishes of the given stage via corresponding conduits, wherein each conduit is fluidly connected to an interior of the petri dish in the given stage.

15. The carousel system of claim 13, wherein the base frame has a slot for each petri dish and the slot is configured to receive a light element.

16. The carousel system of claim 15, further comprising:

plural light elements configured to be removably attached to the slots in the base frame with spring-loaded pins.

17. The carousel system of claim 13, further comprising:

plural temperature-controlled elements configured to be attached to the plural petri dishes to control a temperature inside the plural petri dishes.

18. The carousel system of claim 13, wherein each stage has a hexagonal cross-section in a horizontal plane.

19. A method for automatically monitoring plant growth, the method comprising:

placing plural petri dishes into a carousel of a plant monitoring system, each petri dish holding plural seeds;

controlling a number of images taken per hour or minutes by a camera of the plural petri dishes;

rotating the carousel so that each petri dish is imaged by the camera at a given first time interval;

vertically moving the camera so that each stage of the carousel is imaged by the camera at a given second time interval, wherein the stages are staked on top of each other;

providing light to each petri dish in the carousel, where a duration of the light, and a wavelength of the light are dynamically selected by a control subsystem;

supplying water to the petri dishes first stage of the carousel; and controlling a temperature of the petri dishes in a second stage of the carousel with plural temperature-controlled elements.

20. The method of claim 19, further comprising:

applying a first algorithm to the acquired images of the seeds to determine seed locations in the petri dishes;

applying a second algorithm to the acquired images to determine pixels locations associated with roots of the seeds; and calculating the root length for each plant and germination rate.

* * * * *